United States Patent [19]
Macri et al.

[11] Patent Number: 5,920,871
[45] Date of Patent: Jul. 6, 1999

[54] METHOD OF OPERATING A GENERAL PURPOSE DIGITAL COMPUTER FOR USE IN CONTROLLING THE PROCEDURES AND MANAGING THE DATA AND INFORMATION USED IN THE OPERATION OF CLINICAL (MEDICAL) TESTING AND SCREENING LABORATORIES

[76] Inventors: Vincent J. Macri; Rebecca Clark; Patricia Tricamo, all of c/o Equichem Research Institute Ltd., P.O. Box 491, Durham, N.H. 03824-0491; James N. Macri, 170 Sidney St., Oyster Bay, N.Y. 11771

[21] Appl. No.: 08/288,669

[22] Filed: Aug. 9, 1994

Related U.S. Application Data

[63] Continuation of application No. 08/136,208, Oct. 15, 1993, abandoned, which is a continuation-in-part of application No. 07/736,959, Jul. 29, 1991, abandoned, and application No. 07/709,019, May 31, 1991, Pat. No. 5,258,907, which is a division of application No. 07/420,775, Oct. 12, 1989, abandoned, which is a continuation-in-part of application No. 07/360,603, Jun. 2, 1989, abandoned.

[51] Int. Cl.$^6$ .................................................. G06F 17/30
[52] U.S. Cl. ........................................................ 707/104
[58] Field of Search ........................................ 436/518, 548, 436/808; 364/413.07, 413.08, 413.11, 413.01; 395/615, 20–3; 435/7.92, 320.1; 514/292, 818

[56] References Cited

U.S. PATENT DOCUMENTS

| | | | |
|---|---|---|---|
| 4,315,309 | 2/1982 | Coli | 364/200 |
| 4,857,716 | 8/1989 | Gombrich | 235/462 |
| 5,229,584 | 7/1993 | Erickson | 235/375 |
| 5,307,262 | 4/1994 | Ertel | 364/413.01 |
| 5,356,817 | 10/1994 | Cole | 436/64 |
| 5,465,082 | 11/1995 | Chaco | 340/825.54 |
| 5,557,514 | 9/1996 | Seare | 395/202 |

OTHER PUBLICATIONS

TM Reynolds, The Mathematical basis of multivariate risk screening with special reference to screening for Down's Syndrome associated pregnancy (Ann Clin Biochem 1989; 27: 452–458.

NJ Wald, Maternal serum screening for Down's Syndrome in early pregnancy (BMJ vol. 297, Oct. 8, 1988, pp. 883–887.

NJ Wald, Maternal Serum unconjugated oestriol as an antenatal screening test Down's Syndrome (BJOG, Apr. 1988, vol. 95, pp. 334–341).

Amniotic fluid and plasma concentrations of pregnancy–associated plasma protein (PAPP–A) Throughout pregnancy: comparison with other fetoplacenta products. by P. Bischof et al. British Journal of Obstetrics and Gynaecology, pp. 358–363 May 1982.

Methods of Information in Medicine. by MCM MacIntosh, Predicting Fetal Chromosome anomalies in First Tri semester Using Pregnancy Associated Plasma Protein–A: A Comparison of Statistical Methods, pp. 175–179 Feb. 1993 vol. 32.

*Primary Examiner*—Thomas G. Black
*Assistant Examiner*—Diane D. Mizrahi
*Attorney, Agent, or Firm*—Fish & Richardson P.C.

[57] ABSTRACT

A digital computer system in a clinical testing laboratory assays free Beta in a biological sample obtained from a pregnant patient and uses the resulting data, along with other patient and reference data, to create a patient profile. Operations of the system include inputting patient data for a pregnant patient into an electronic memory and creating an individual profile for each patient. The processor assigns specific accession numbers for each specimen, creates an assay format for a biological sample, and interfaces with the assay equipment to control the assaying of the biological sample for free Beta. The assay results are communicated into memory in machine readable form and used along with patient data and reference data to calculate a patient specific risk that the patient is carrying a fetus having a designated defect. From all the input data, the processor creates comprehensive patient profiles in both machine readable form and human readable form.

18 Claims, 19 Drawing Sheets

HARDWARE OVERVIEW

HARDWARE OVERVIEW

PROGRAM OVERVIEW

PATIENT DATA ENTRY

CREATE ASSAYS AND ENTER TEST RESULTS

IMPORT ASSAY DATA

CREATE/PRINT REPORTS

EDIT/VIEW PATIENTS

STATISTICAL REPORTS

PHYSICIAN OPTIONS

CHANGE REFERENCE DATA

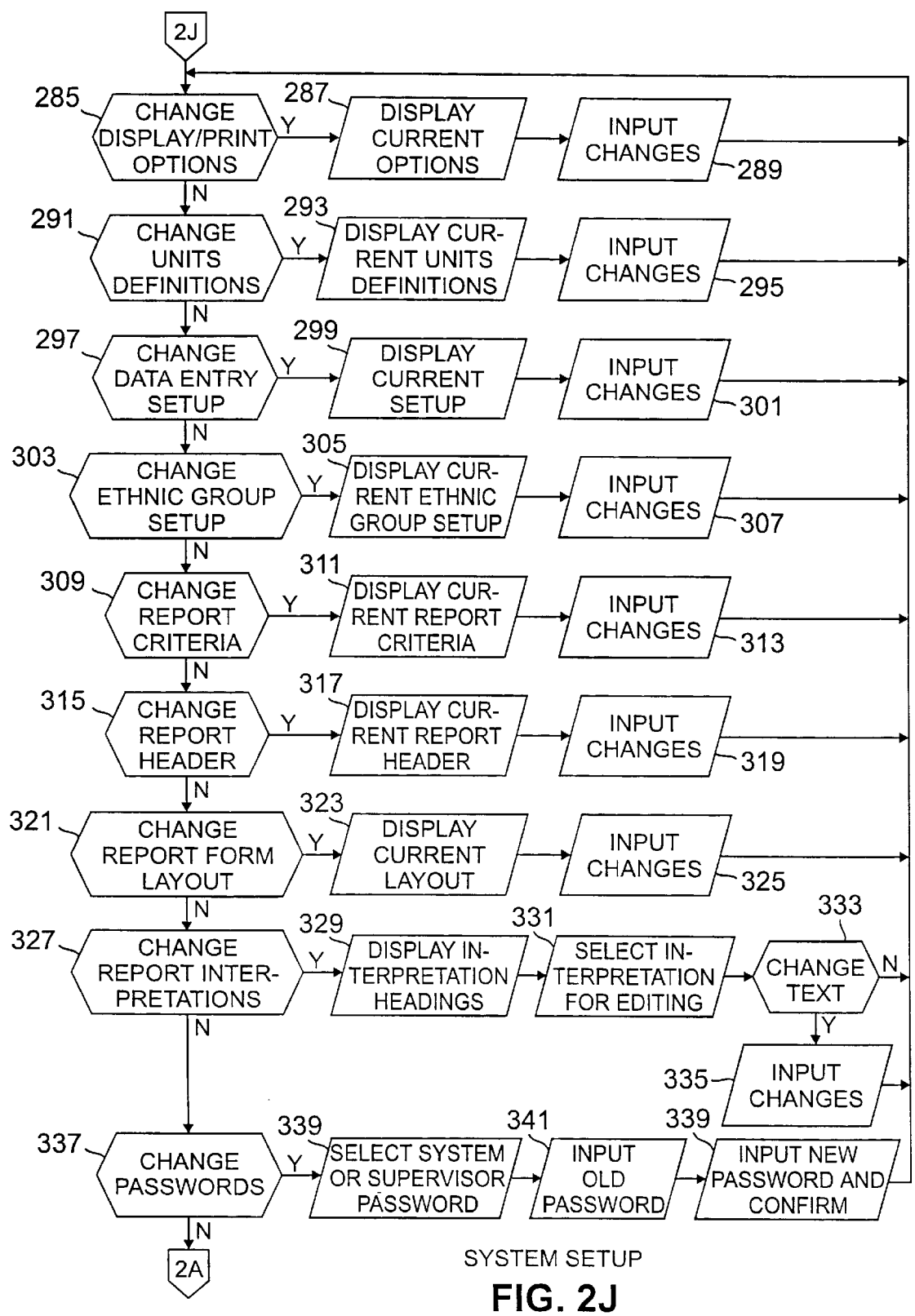
FIG. 2J — SYSTEM SETUP

ARCHIVE RECORDS

METHOD OF OPERATING A GENERAL PURPOSE DIGITAL COMPUTER FOR USE IN CONTROLLING THE PROCEDURES AND MANAGING THE DATA AND INFORMATION USED IN THE OPERATION OF CLINICAL (MEDICAL) TESTING AND SCREENING LABORATORIES

This application claims priority under 35 USC §120 as a continuation of U.S patent application No. 08/136,208, filed Oct. 15, 1993 and now abandoned; which is a continuation-in-part of U.S. patent application No. 07/736,959 filed Jul. 29, 1991 and a continuation-in-part of U.S. patent application No. 07/709,019, filed May 31, 1991 now U.S. Pat. No. 5,258,907; which is a divisional of U.S. patent application No. 07/420,775, filed Oct. 12, 1989and now abandoned; which is a continuation-in-part of U.S. patent application No. 07/360,603, filed Jun. 2, 1989 and now abandoned.

FIELD OF THE INVENTION

The present invention pertains to a method of operating a general purpose digital computer system for use in controlling the laboratory procedures and managing the data and information used in the operation of clinical testing laboratories. More particularly, the present invention pertains to computer methods for controlling and monitoring immunochemical assay operations and for inputting, processing, reducing, manipulating and producing prenatal screening (testing) laboratory data and information in laboratories assaying for free Beta (hCG) as well as other biochemical substances.

BACKGROUND OF THE INVENTION

Prenatal screening (i.e. presymptomatic testing of pregnant patients) is utilized in developed countries to determine whether a pregnant woman's probability, i.e. risk, of carrying a fetus with certain conditions, such as chromosomal abnormalities and/or physical defects, warrants the risks associated with proceeding to undergo invasive diagnostic procedures. The specific conditions screened for in prenatal screening programs include but are not limited to:

(1) Neural Tube Defects [NTDs] (e.g. Anencephaly, Open Spina Bifida),
(2) Ventral Wall Defects [VWDs], and
(3) Chromosomal Anomalies such as Down Syndrome [DS], Turner's Syndrome, Trisomy 13, Trisomy 18 and others.

Generally, a biological sample, such as a blood or urine sample, is obtained from a pregnant woman by her physician, or by a nurse or technician in her physician's office, during a prenatal examination. The biological sample is then sent to a clinical laboratory for analysis, together with background data on the pregnant woman and documents specifying the types of analyses the physician would like the clinical laboratory to perform.

Clinical laboratories may receive a large number of biological samples on a daily basis. In order to ensure that each sample is correctly handled, and analyzed in accordance with the pregnant woman's and physician's wishes, clinical laboratories need to have a system for tracking the sample, together with any accompanying documents or background data, for the period of time the sample remains in the laboratory.

In prenatal screening, biological samples, such as a blood or urine samples, are obtained from pregnant women and analyzed to quantify the level of specific substances, referred to as "analytes". The level of each analyte in the biological sample is generally determined by assaying the sample using appropriate monoclonal or polyclonal antibodies and reagents. In order to ensure that the proper types of reagents and antibodies are available on a daily basis, it would be desirable for the clinical laboratory to have a system for inventory control. In addition to including antibodies and reagents, the inventory control system may also include the other supplies necessary for operating a clinical laboratory, including, but not limited to, glassware, assay plates, pipettes, paper, writing instruments, and the like.

Common analytes measured in prenatal screening include, but are not limited to alpha-fetoprotein (AFP), unconjugated estriol (UE), human chorionic gonadotropin (hCG), and more recently, the free beta (hCG) protein ("free Beta") and PAPP-A. Prenatal screening utilizing these analytes, and in particular free Beta, is described in co-pending U.S. patent application No. 07/925,844, filed Aug. 6, 1992, the disclosure of which is hereby incorporated by reference.

In a prenatal screening protocol, the levels of an individual patient's analytes are compared to reference data in order to determine the pregnant woman's risk of carrying an "affected" fetus. The reference data comprises:

the levels of the analytes in pregnant women carrying a fetus with the particular condition ("affecteds"),
the levels of the analytes in pregnant women carrying a fetus without the condition ("unaffecteds"),
the prevalence of the condition in the overall population, and
patients' clinical data.

In general, reference data are obtained from retrospective studies of unaffected and affected deliveries for each week of gestation from approximately, but not limited to, 10–22 weeks.

Certain personal ("clinical") information pertaining to the patient may also be incorporated into the comparison, including but not limited to, the gestational week (referred to as GA for gestational age) of the pregnancy as well as the pregnant woman's age, race or ethnicity, weight, area of residence, family history of birth defects, and/or other medical information such as insulin-dependence for diabetes.

In the field of prenatal screening, computer software systems have been developed that perform analyses using data obtained from biological samples (e.g., blood) obtained from pregnant women and the patients' clinical data. These software systems generally compare levels of specific substances within the sample to reference data (described above) to determine the pregnant woman's risk of carrying a fetus with a Neural Tube Defect (NTD) or Down Syndrome (DS). Examples of other computer software systems are:

(1) Alpha, by Prosig (USA) Inc., P.O. Box 377, Rockaway, N.J. 07866,
(2) AFP-Expert, by Benetech Medical Systems, 176 St. George Street, Toronto, Ontario Canada M5R 2M7,
(3) AFP/Sample Management Software, by Robert Maciel Associates, Inc., Arlington, Mass.,
(4) Prenval, by Base Ten Systems, Trenton, N.J., and
(5) Dermalog, in Germany.

The reference data in these known systems is set when the systems are manufactured and are generally not modifiable by the user.

The presence of fixed reference data presents a problem for the user since the distribution of analyte levels measured by laboratories typically changes over time due to the racial composition of the pregnant population, geographic location of the patients served, shifts of the patient population, variation within the blood specimens themselves, modification in laboratory techniques, or combinations of such causes. The prevalence of birth defects within the general population can also alter over time. When users are able to define their own reference data, the laboratory analyzing system is better able to adapt to changes in its patient database and to provide analytical test results with increased precision for each individual patient.

The pregnant woman's risk of carrying an "affected" fetus is generally reported back to the patient's physician (primary care provider). The clinical laboratory then bills the primary care provider, or the patient's insurance provider for the cost of the screening. It would be is desirable for a clinical laboratory to have a finance and accounting system which receives billing/insurance information regarding the patient, and a description of the screening protocols which have been performed using the patient's biological sample, directly from the system utilized by the laboratory to analyze the sample.

The above is a brief description of some deficiencies in disclosed prenatal analysis systems which are overcome by the present invention, and a brief description of features that would be advantageous in the management of a prenatal screening laboratory and are achieved by the present invention. Other features, advantages, and embodiments of the invention are set forth in the following description, accompanying drawings, and appended claims.

SUMMARY OF THE INVENTION

The present invention provides a computer software method and system for laboratories for use in controlling the laboratory procedures and managing the data and information used in the operation of clinical testing laboratories. More particularly, the present invention pertains to computer methods for controlling and monitoring immunochemical assay operations and for inputting, processing, reducing, manipulating and producing prenatal screening (testing) laboratory data and information in laboratories assaying for free Beta as well as other biochemical substances. The system of the present invention also provides for an interface between laboratory analysis data and information and the laboratory's inventory control system and the laboratory's finance and accounting system.

The present invention provides a method of operating a general purpose digital computer system having a plurality of data files to operate and manage a prenatal screening laboratory comprising a plurality of the following features:

a) means for inputting and storing patient data including patient clinical information and billing information;
b) means for creating analyte runsheets;
c) means for creating a format for analyte runsheets;
d) means for interfacing with laboratory equipment to import assay data;
e) means for calculating patient risks for one or more anomalies selected from the group consisting of: NTDs, VWDs, Down Syndrome, Turner's Syndrome, Edward's Syndrome and Trisomy 13;
f) means for producing patient reports in electronic form;
g) means for creating a database of patient records including patient data and screening data including assay data and patient risks;
h) means for interfacing with a printer to print selected patient reports;
i) means for searching patient records including patient reports and patient data;
j) means for revising and recalculating patient results based on changes in patient's clinical information;
k) means for performing statistical analyses of information contained in the database of patient records;
l) means for creating a database of physicians participating in a screening protocol;
m) means for defining reference data for each analyte for serum (blood) and/or amniotic fluid;
n) means for defining a method of interpolating medians;
o) means for incorporating adjustments for maternal weight, insulin dependence, or multiple pregnancy into the patient's risk calculation;
p) means for defining prevalence data for each condition;
q) means for providing security passwords;
r) means for archiving portions of the patient database;
s) means for interfacing with interfacing with an accounting database; and
t) means for printing patient bills.

Each of these features are more fully described in the following paragraphs.

The present invention includes means for inputting and storing patient data including patient clinical information and billing information. The means for inputting data may include a physical apparatus such as a keyboard or mouse. Patient data may also be input electronically through an interface between the location where the biological sample is obtained from the patient, and the laboratory. For example, patient data may be transmitted in machine readable form over a telephone line connecting the physician's office and the laboratory. Patient data as used herein, includes, but is not limed to: clinical and personal background data on a patient, such as the data described below; and billing information, which may include information relating to the patient's insurance carrier, if any. The means for storing patient data include the memory of the CPU as described below, as well as means for formatting and catalog patient data to permit its easy retrieval.

The means for creating analyte runsheets, and the means for creating a format for analyte runsheets, are explained more fully below in the detailed description of the invention.

The means for interfacing with laboratory equipment to import assay data may include means for transferring electrical data in machine readable form such as computer cables and the like. The interface between the computer(s) running the system of the present invention and the laboratory equipment should allow for data from the laboratory equipment to be directly input into the system of the present invention.

In the description of the present invention contained herein, reference is made to clinical assays performed by laboratory equipment on a biological sample. As will be recognized by those of ordinary skill in the art, the system of the present invention may be utilized with data from many types of analyses performed by a laboratory on biological samples, including, but not limited to: recombinant DNA technology; in-situ PCR (polymerase chain reaction); immunogold-silver techniques as well as traditional immunological assays utilizing antibody reactions. Thus, the term "assay" as used herein should be construed broadly and the present invention should not be construed as limited to utilization only in clinical laboratories performing immunological assays.

The means for calculating patient risks for anomalies selected from the group consisting of: NTDs, VWDs, Down Syndrome, Turner's Syndrome, Edward's Syndrome and combinations thereof are described more fully below in the detailed description of the invention.

The means for producing patient reports in electronic form are explained more fully below and should allow patient reports to be electrically transmitted to a printer to produce hard copy, and also allow patient reports to be electrically transmitted to an off-site location, such as a physician's office.

The means for creating a database of patient records including patient data and screening data including assay data and patient risks include but are not limited to any of the commercially available database programs such as File-Maker Pro, by Claris, DBase, Foxbase, and the like.

The means for interfacing with a printer to print selected patient reports include computer cables or other means for electrically connecting a printer and a CPU, as well as printer driver software.

The means for searching patient records including patient reports and patient data include means for entering search terms and means for connecting a Boolean search or the like.

Means for revising and recalculating patient results based on changes in patient's clinical information allow a user to re-run the screening protocol if information relating to the patient has changed Means for performing statistical analyses of information contained in the database of patient records include, but are not limited to, any of the commercially available computer programs for statistical analysis, such as SAS, or SPSS.

Means for creating a database of physicians participating in a screening protocol include but are not limited to any of the commercially available database programs such as File-Maker Pro, by Claris, DBase, Foxbase, and the like.

Means for defining reference data for each analyte for serum (blood) and/or amniotic fluid are discussed more fully below, and allow a user to customize the screening protocol to produce more accurate results.

Means for defining a method of interpolating medians; means for incorporating adjustments for maternal weight, insulin dependence, or multiple pregnancy into the patient's risk calculation; and means for defining prevalence data for each condition relate to the patient's risk calculation and are discussed more fully in the following sections.

Means for providing security passwords include but are not limited to commercially available computer software for providing system security.

Means for archiving portions of the patient database include but are not limited to computer software which will archive at specified time intervals. The software may also include means for compressing the archived records to reduce the amount of memory space needed for storage.

Means for interfacing with an accounting database and means for printing patient bills include means for producing patient reports, and patient screening information in electronic form in a manner which allows the data to be read by a laboratory's accounting software (time/billing software). The accounting software may include means for directly printing patient bills, in a format requested by the patient, the patient's physician and/or the patient's insurer.

The present invention allows users to define system parameters including units of measurement, log base (used in result calculations), cut-off levels for increased risk results, separate medians for different ethnic groups ,below sensitivity limits for AFP/free Beta, range of gestational weeks acceptable for specimens, order of listing information fields in the patient data entry screen, definition of patient identification codes (sample number and hospital number), date format, printer type, printer paper size, report format (choice of 4) and text to appear on patient reports as the header and the signature line.

The present invention produces patient reports in electronic form, which may be transmitted to a printer, or sent electronically (via facsimile or modem) directly to physicians, hospitals or patients. Information from the patient reports may be utilized to produce pregnancy outcome letters to physicians, The method and system of the present invention advantageously enable the user to define the statistical distribution parameters and prevalence data utilized in prenatal screening for both fetal neural tube defects (NTDs) and fetal chromosomal abnormalities. The method and system of the present invention are particularly well suited for use in a screening protocol utilizing free Beta, which has been shown to be a superior marker for the prenatal detection of chromosomal anomalies and other known anomalies compared to the intact hCG molecule. The method and system is also particularly well suited for use in a prenatal Down Syndrome screening protocol and for use in diagnostic testing for amniotic fluid alpha-fetoprotein (AFAFP).

The computer software method and system of the present invention enables the user to enter patient clinical data and to record these important data such as gestational age, maternal age, maternal weight, patient's name, and whether or not the patient has had a prior NTD, VWD, or DS pregnancy, or other anomaly, such as a fetus with Edwards Syndrome or Turner's Syndrome. The system also provides for identifying data entry with respect to the patient's physician and physicians participating in the screening program. The system further provides for data entry relating to the patient's billing and/or insurance information. All patient data can be output to a display, modified, or output to a printer.

For each batch of patient biological samples (patient specimens) a runsheet can be generated for free Beta, AFP, etc. testing. A runsheet lists which samples to run and in what order. Also, labels can be printed for each specimen container in order to assist in tracking individual specimens. Risks can be calculated based on all entered data from one or more file databases. Such data is used to determine whether the results obtained from an individual sample indicate an increased risk of an NTD, DS, or other prenatal condition. The normative data can also be displayed and modified by the user, which allows for greater flexibility and greater accuracy.

In addition to the advantages described in the preceding paragraphs, the computer software method and system of the present invention include the following advantages in comparison with the software packages set forth above:

i) the system of the present invention may be specifically tailored for use in a screening protocol utilizing AFP and free Beta;

ii) the system of the present invention allows a user to set the population parameters utilized in the generation of a patient specific risk;

iii) the system of the present invention allows a user to define the apriori risk of an NTD, VWD or Chromosomal Anomalies such as Down Syndrome [DS], Turner's Syndrome, Trisomy 13, Trisomy 18 (Edward's Syndrome) and others; at various gestational ages;

iv) the system of the present invention allows for specific risk calculation in twin pregnancies;

v) the system of the present invention allows the generation of customized patient reports, the encoding of these reports into the system database;

vi) the population parameters, and the reference data, utilized in the system of the present invention include levels of free Beta in affecteds and unaffecteds; and vii) the system of the present invention is user friendly.

Further advantages of the computer software method and system of the present invention will become apparent from the following more detailed description.

BRIEF DESCRIPTION OF THE DRAWINGS

FIGS. 2A–2L is a flowchart of the system of the present invention.

DETAILS DESCRIPTION

Figure 1:
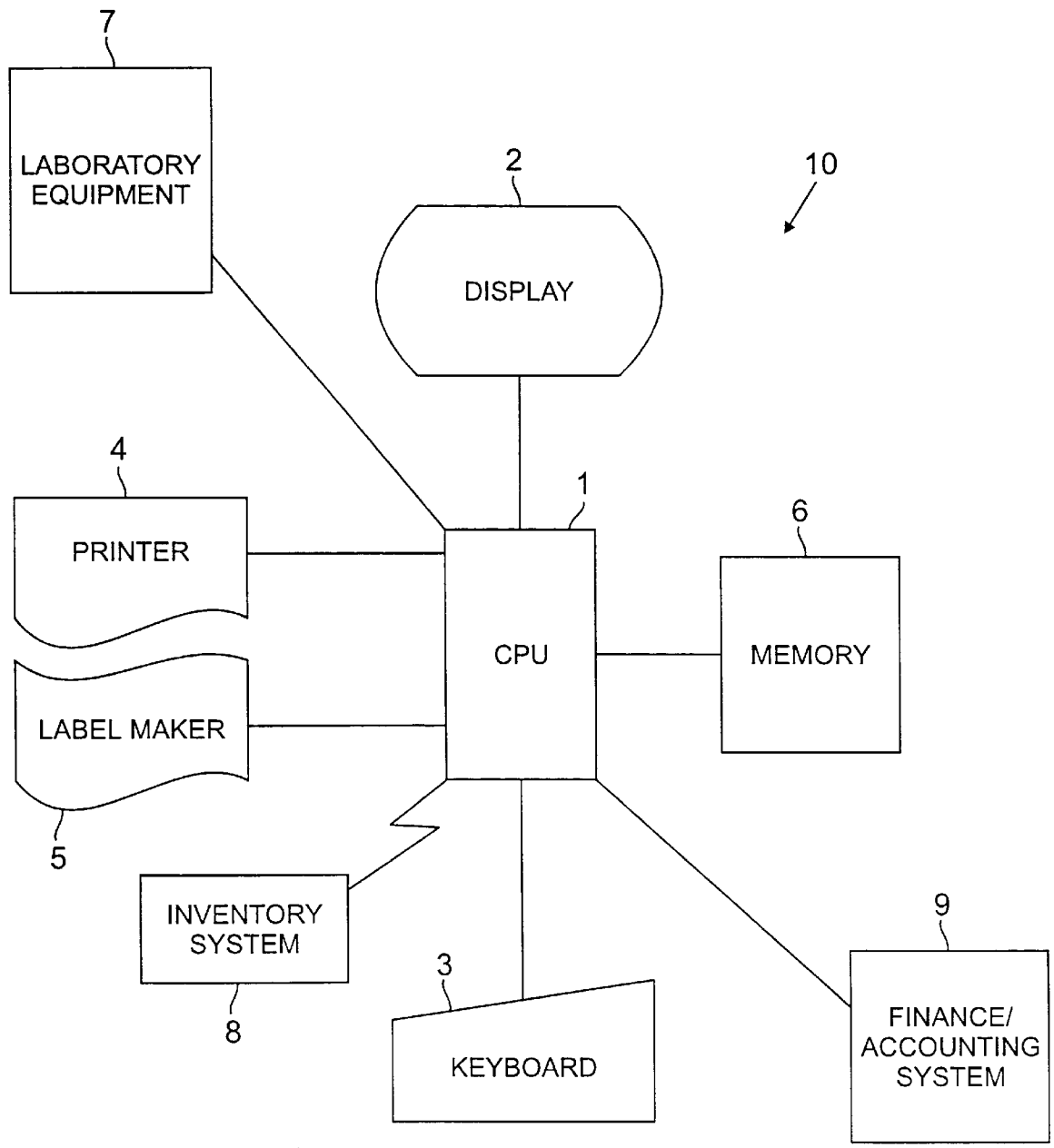
FIG. 1 is a block diagram of a prenatal screening system constructed according to the present invention.

Referring to FIG. 1, a block diagram of a method and system for the operation and management of a clinical laboratory, 10 constructed according to the present invention is shown. The system comprises one or more Central Processing Unit(s) (CPU), 1 which can be, but is not limited to, a microcomputer (such as a Personal Computer or PC) operating with an Intel 80X86 microprocessor or a Motorola 680X0 processor (wherein X is an integer, greater than or equal to 0, i.e. Intel 80086, Intel 80186, Motorola 68000, Motorola 68010 etc ). The CPU, 1 is electronically coupled to at least one display, 2, such as a CRT screen, for displaying retrieved information and prompting a user for the input of information. The CPU, 1 is also coupled to at least one input device, 3, such as a keyboard or mouse, for the input of information from the user, at least one printer, 4 for printing information in hard-copy format, and/or at least one label maker, 5 for printing labels for specimen containers (described below). As will be understood by those of ordinary skill in the art, labels may be printed on printer, 4. Computer memory, 6 is provided, electronically coupled to the CPU, 1 for the storage of patient and physician data. The system of the present invention is advantageously configured such that laboratory equipment, 7, utilized for the assaying and immunological analysis of patient biological samples, electrically interfaces with CPU, 1 as shown in FIG. 1. In addition, the system of the present invention is additionally configured such that CPU, 1 interfaces with a laboratory's finance and accounting system, 9 to permit the finance and accounting records to be updated with information from the database of patient records. Still further, the system of the present invention is advantageously configured such that CPU, 1 interfaces with a laboratory's inventory control system, 8. In this manner, inventory records can be updated each time a patient's sample is analyzed.

Figure 2A:
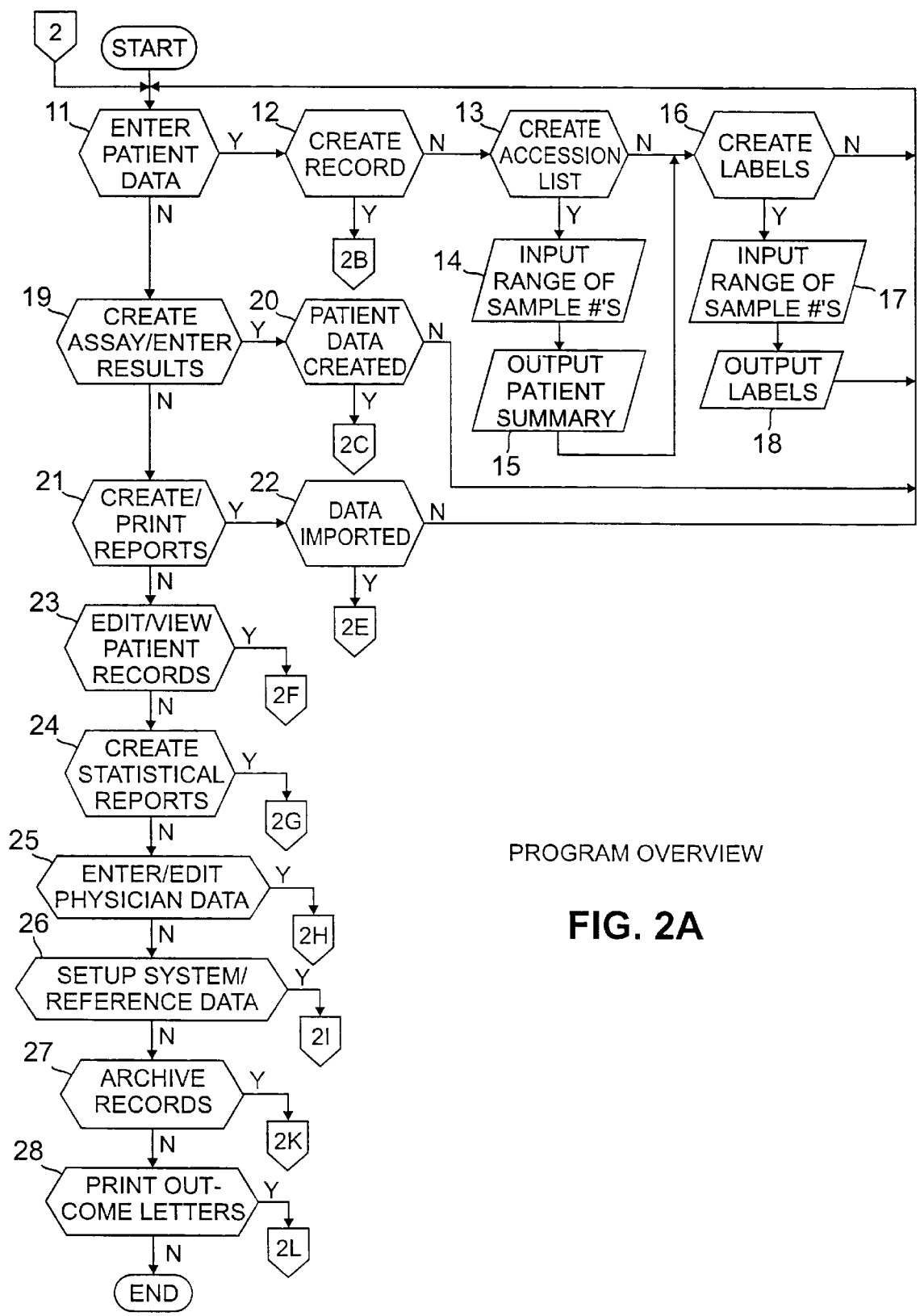

Referring to FIG. 2A–2L, a flowchart for the operation of the system of the present invention is shown. FIG. 2A shows a general module selection scheme, where a plurality of user selected modules are shown. If the user selects data entry in decision block 11, then control of the system switches to the data entry module. If the user desires to create a record in decision block 12, then control passes to the method depicted in FIG. 2B where patient data can be entered at the input device, 3.

Figure 2B:
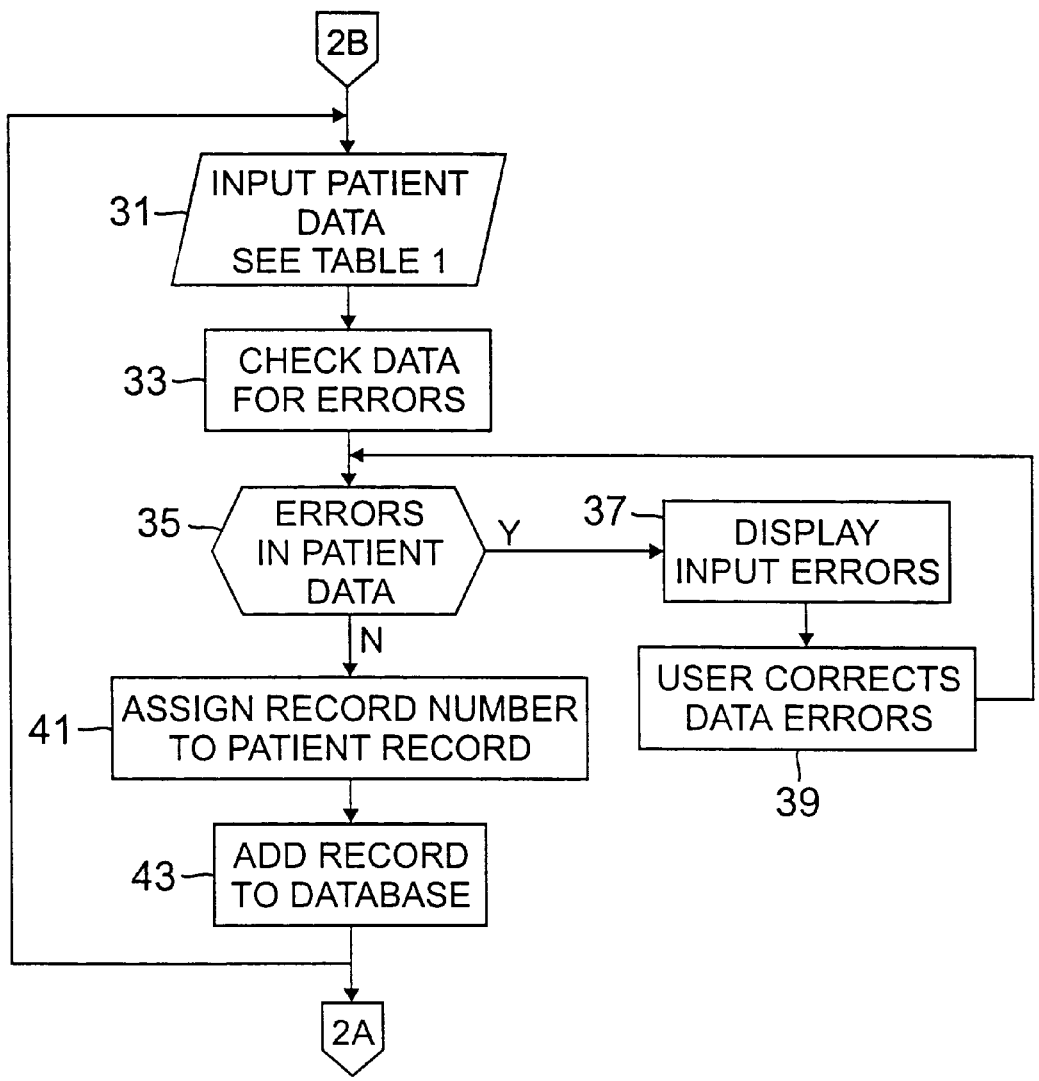

Referring to FIG. 2B, the data entry is shown for the input of descriptive data for each patient. In block 31, the user inputs a variety of information such as the fields listed in Table I.

TABLE I

| | |
|---|---|
| Hospital Number | LMP/US/EXAM Ind. |
| Surname | No. of Fetuses |
| First Name | Maternal Weight |
| Age at EDC* | Gravida |
| Date of Birth | Para |
| Ethnic Group # | Insulin |
| Physician Code | Bleeding |
| Specimen Type | Smoking |
| Date Collected | Previous NTD |
| LMP | Previous Downs |
| GA by US/EXAM | Free Beta |
| Date of US/EXAM | Previous Result |
| | Sample Number |

*EDC is an abbreviation for estimated date of confinement, i.e. the term of art for the pregnant woman's delivery date.

The individual fields listed in Table I are described below:

Hospital Number the patient's hospital number (a combination of 8 letters and numbers can be entered). This is an index field, and patient records can be searched using their hospital numbers. The name of this field can be redefined by the user.

Surname: the patient's last name (e.g., up to 15 characters).

First Name: the patient's first name or names (e.g., up to 14 characters).

Age at EDC and Date of Birth: If patient's date of birth (DOB) is entered, the system automatically calculates the patient's age at EDC. If only maternal age (in years) is entered, the system assumes age at EDC is equal to maternal age. As will be understood by those of ordinary skill in the art, it is possible to configure the program to utilize EDD (estimated date of delivery) instead of EDC. EDD involves exactly the same calculations as EDC. Only the name of the field would need to be changed.

Ethnic Group: a number (e.g., 1 to 8) indicating the race or ethnicity of the patient. When the system is initialized, codes can be assigned to a maximum of 8 ethnic groups by the user. The names of the ethnic groups are also defined by the user.

Physician Code: a code (e.g., a 4 digit number) defined by the user indicating the physician responsible for the testing of the patient. The name and address can be stored in memory and later retrieved and displayed based on the entered physician code.

Specimen Type: an indication of whether the specimen(s) taken from the patient is (are) blood (centrifuged into serum), amniotic fluid, or both serum and fluid. If both serum and fluid specimens are taken from the same patient, the system creates two patient records, one for serum and one for fluid, and assigns a unique record number to each (see below).

Date Collected: the date the specimen was drawn from the patient.

LMP: the date of the patient's last menstrual period (LMP).

GA by US/EXAM: the gestational age (GA) of the pregnancy. If GA is based on LMP, this field can be automatically determined by the system. If GA has been determined by Ultrasound (US) or by Physical Examination (EXAM), this field must be entered by the user.

Date of US/Exam: the date on which the Ultrasound (US) or Physical Examination (EXAM) test for gestational age (GA) was performed.

LMP/US/EEAM Ind.: a number from 0–2 indicating whether the gestational age is based on LMP (0), US (1), or EXAM (2).

No. of Fetuses: whether the patient is carrying multiple fetuses [Y/N].

Maternal Weight: maternal weight in kilograms or pounds.

Gravida. the total number (1–9) of pregnancies including the current pregnancy. If the total number of pregnancies is greater than 9, the number 9 is entered in this field.

Para: the total number of living children (1–8) borne by the patient. In this usage "living children" means alive at the time of testing. If the total number is greater than 8, the number 8 is entered in this field.

Bleeding: whether vaginal bleeding has occurred during the pregnancy [Y/N].

Insulin: whether the patient is an insulin dependent diabetic [Y/N]. Gestational diabetics are not insulin dependent diabetics.

Smoking: whether the patient is a significant smoker [Y/N].

Previous NTD: whether the patient has had a previous child with NTD [Y/N].

Previous DS: whether the patient has had a previous child with Down Syndrome (DS) [Y/N].

Free Beta: whether measurement for free Beta will be performed on the maternal serum (blood) specimen [Y/N]. The system assumes that AFP will be measured on every specimen.

Previous Result: denotes whether a prior screening specimen for the same pregnancy indicated an elevated AFP or an increased risk of Down Syndrome.

Sample Number a code (e.g., a 4 digit number) defined by the user for internal lab control. This is an index field, and patient records can be searched using their sample numbers. The name of this field can be redefined by the user.

The types of data set forth in Table I may be divided into several distinct groups:
1) Identification data—assisting the user in identifying the patient, the treating physician/hospital, and the specimens taken from the patient;
2) Attribute data—relating to the patient's age, maternal age, ethnic background, etc.; and
3) Diagnostic data—relating to what specimens are taken from the patient and properties thereof.

Once the user has input data into the prenatal screening method and system of the present invention, the system checks the data in block 33 to insure that it conforms to field definitions (e.g., "Y" or "N" inputs for fields such as Insulin and Previous NTD or DS, proper date form for Date of Birth and US/EXAM, etc.). Data that has been entered mistakenly (see decision block 35) is redisplayed (see block 37) for correction (see block 39) until the input data is in proper form. The system then assigns a unique record number to the patient record just created and adds the record to the database (see blocks 41, 43). The record number is a number assigned by the system which corresponds to the order in which the patient record was entered into the system, i.e. record number 1 is the first record ever entered into the system. If both serum and fluid specimens are taken from the same patient, the system creates two patient records, one for serum and one for fluid, and assigns a unique record number to each.

Other options in the data entry module include:
(1) The user can print out a summary of patient data for a specified range of sample numbers (see decision block 13 in FIG. 2A and blocks 14 and 15). The list will contain all patient records which were entered in the Patient Data Entry option between the two sample numbers specified—the list will be in order by record number (i.e. in accession order). The list will contain each patient's sample number, surname, first initial physician code number, date of specimen receipt, date of specimen collection, type of specimen (S=serum, F=fluid), gestational age, method of gestational dating, and tests ordered.
(2) The user can print labels at a label maker (Element #5 in FIG. 1) or printer (Element #4 in FIG. 1) for a specified range of sample numbers. Each label contains the patient's sample number, specimen type (S=serum, F=Fluid), surname, and first initial. Matching labels may be placed on specimen containers or patient documentation (see FIG. 2A, decision block 16 and blocks 17 and 18).
(3) The user can update the surname and hospital number index files (not shown in flowcharts), so that patient data can be accessed by surname and hospital number in other sections of the program.

Figure 2C:
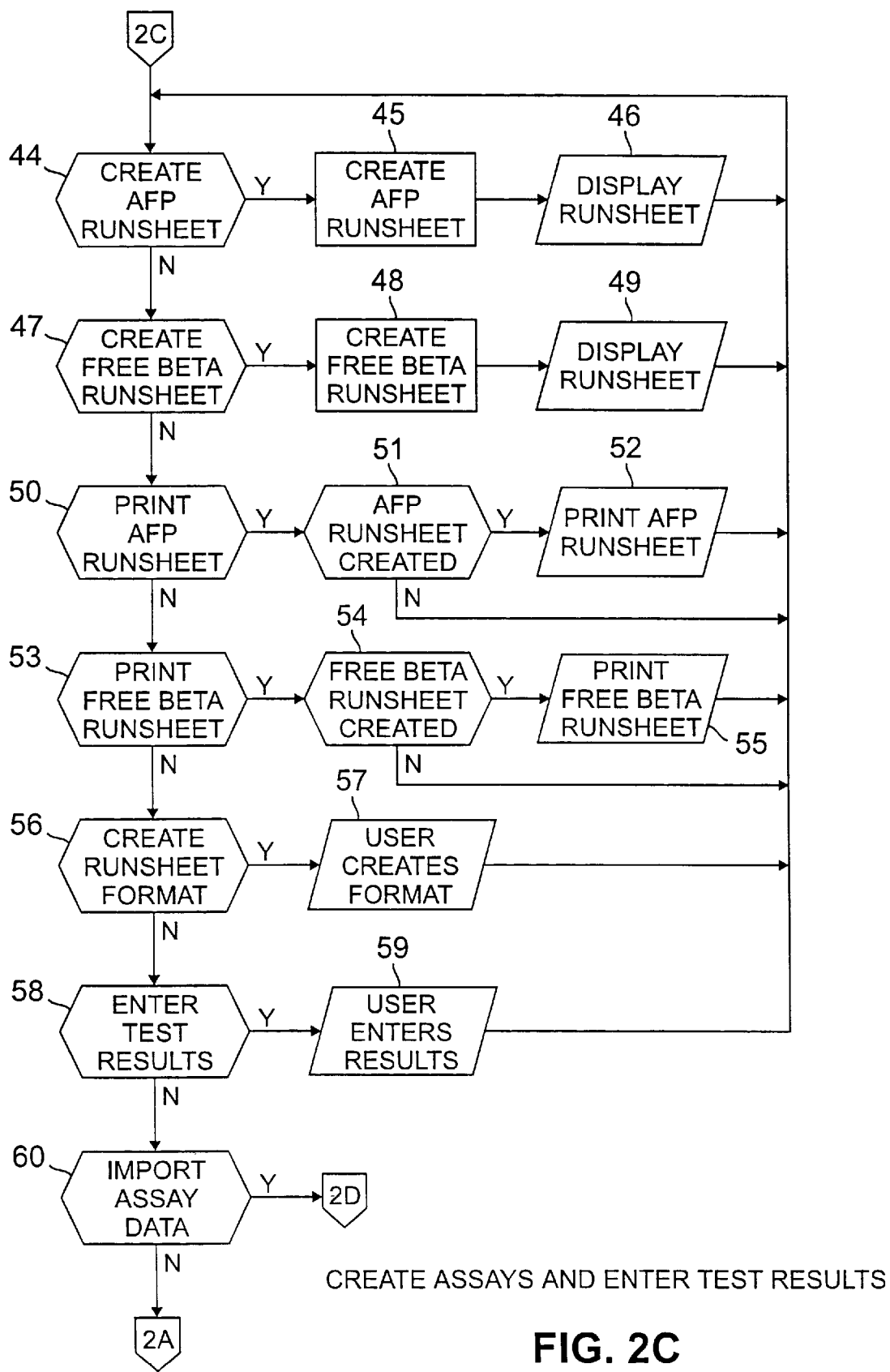
Figure 2D:
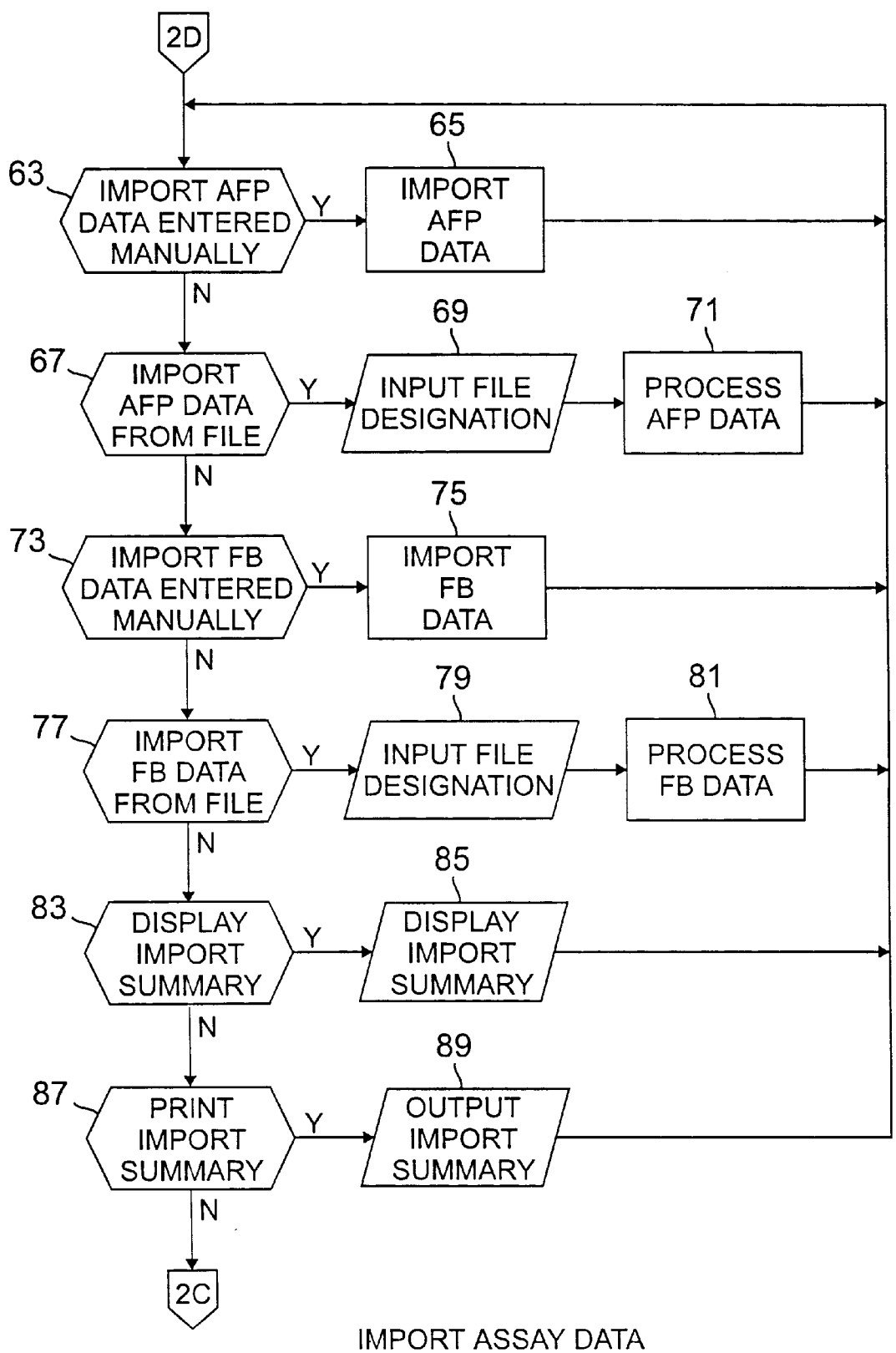

Referring back to FIG. 2A, if the user seeks to perform an assay (laboratory test) or enter test result data (see decision block 19) and patient data has been entered (decision block 20), control passes to decision block 44 (FIG. 2C). Several different assay functions can be performed by the system of the present invention. In decision block 44, if a runsheet is to be created for a serum or fluid AFP test, control passes to block 45, where a runsheet is created. A runsheet indicates which samples are to be run and in what order. When creating a runsheet, the user may choose from a list of runsheet formats designed by the user (see below). The user may also select the number of patient specimens to be included in the runsheet. The final runsheet will be output to the screen (FIG. 1, Element #2) (see block 46).

In a like manner, a runsheet can be created for free Beta serum testing in decision block 47 and blocks 48 and 49. If the user desires, the AFP runsheet created can be printed at a printer (FIG. 1, Element #4) or the like (see decision blocks 50 and 51 and block 52). The user can also print the free Beta runsheet (see decision blocks 53 and 54 and block 55) at a printer (FIG. 1, Element #4). Analyte runsheets which have been created may be edited or deleted from the system. The user may also view a list of analyte specimens for which test results have not been entered.

In another option of the program, the user can create the format to be used in designing analyte runsheets (see decision block 56). In this option, the user selects the number and placement of calibrators, quality control (QC specimens), and patient specimens (see block 57). Formats previously saved may be deleted from the system In a preferred embodiment of the present invention, the assay format designed by a user controls the sequence and number of runs performed by the laboratory equipment utilized to analyze the biological sample.

The user can manually enter assay results (see decision block 58 and block 59) or import them from a data file (see decision block 60). The data file may be created by the laboratory equipment utilized to analyze the sample which may be in electrical communication with the CPU as shown in FIG. 1. The laboratory equipment may also interface with a laboratory's inventory control system to update a database of inventory items, such as reagents, assay plates, pipettes, labels and the like, each time an assay is performed utilizing the laboratory equipment.

Importation of assay results comprises several procedures. If the user desires to import AFP data (decision block 67), the user is prompted to indicate a file containing such data (block 69) stored in the memory (FIG. 1, Element #6). The data contained in the file should be in the following format:

Sample #, AFP, AFP Value, Flag

If the Flag field is non-zero, the data related to that Sample # will not be processed. If the Flag field is 0, the data related to that Sample # will be processed by the system (see block 71).

The user can also import assay data for free Beta (decision block 77). Similar steps are followed as with importing AFP data (see blocks 79 and 81). The data contained in the file should be in the following format:

Sample #, FB, Free Beta Value, Flag

If the Flag field is non-zero, the data related to that Sample # will not be processed. If the Flag field is 0, the data related to that Sample # will be processed.

The user can have a summary displayed (FIG. 1, Element #2) or printed (FIG. 1, Element #4) of the imported data (see decision block 83 and 87). In block 85, the system displays a list of results imported which includes each patient's sample number, specimen type (AFP or free Beta), analyte result, status (flag indicator described above), and importation comment (which sample results were imported, which results were not imported, and which samples need to be redone). In a like manner, the user may print an importation summary at a printer (see block 89). When creating the import summary, the system can distinguish a variety of errors that may occur when importing data, some of which are shown in Table II.

TABLE II

| Error | Reason |
|---|---|
| Not imported | Not "AFP" or "Free Beta" data or the sample # is not on file. |
| Not Imported-Data Field not Empty | The patient record already has a value for the given analyte in the database. This value can be overwritten by going to the Edit/View Patients module. |
| REDO | The Flag was set to a value other than 0. The sample needs to be re-analyzed for the given analyte. |

Finally, in another option of the import menu, test results which were entered manually must be imported (not shown in flowcharts) in order to set up the data so that reports can be generated and the patient database can be updated (see decision blocks 63 and 73 and blocks 65 and 75).

Figure 2E:
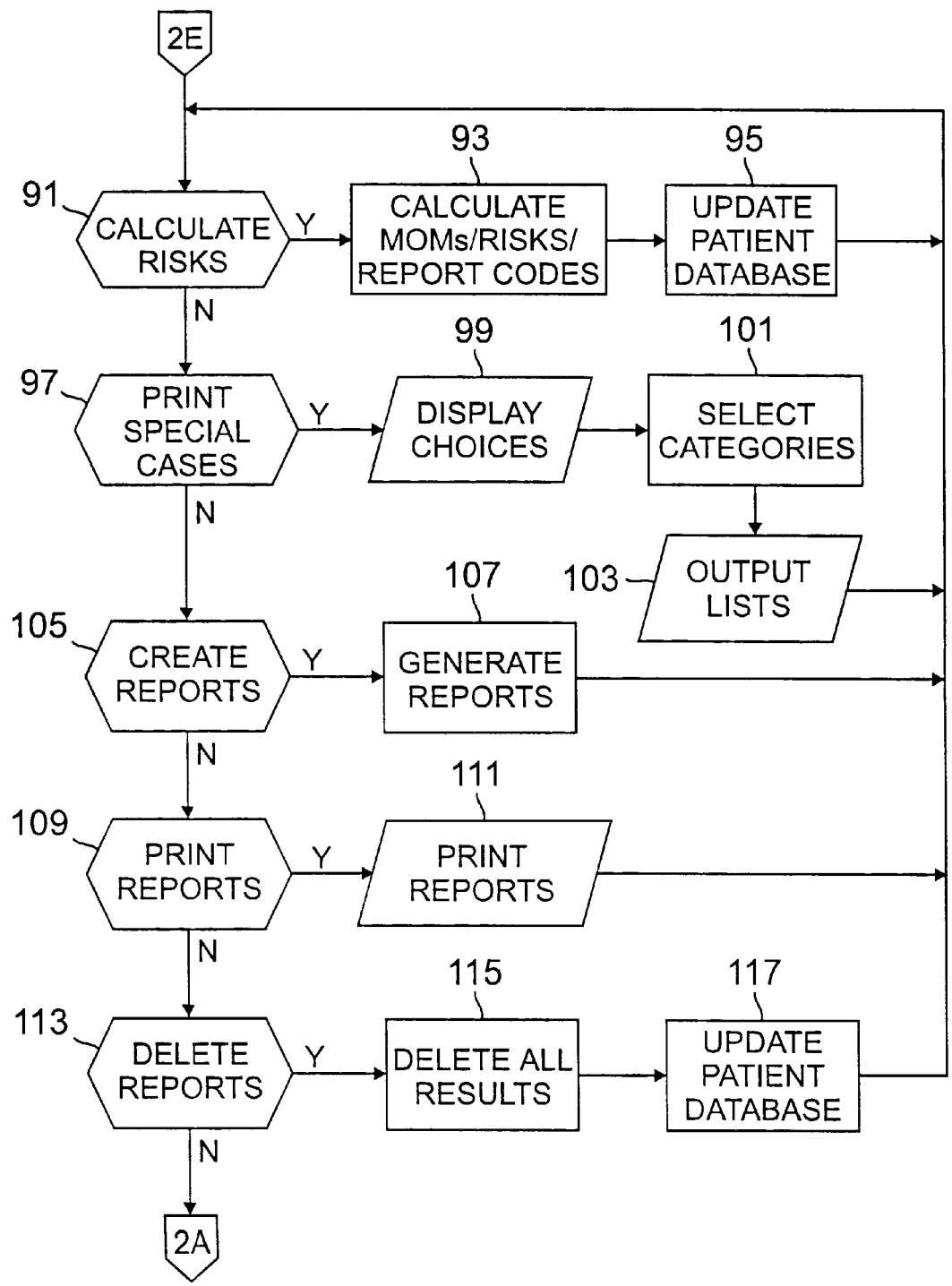
Figure 2F:
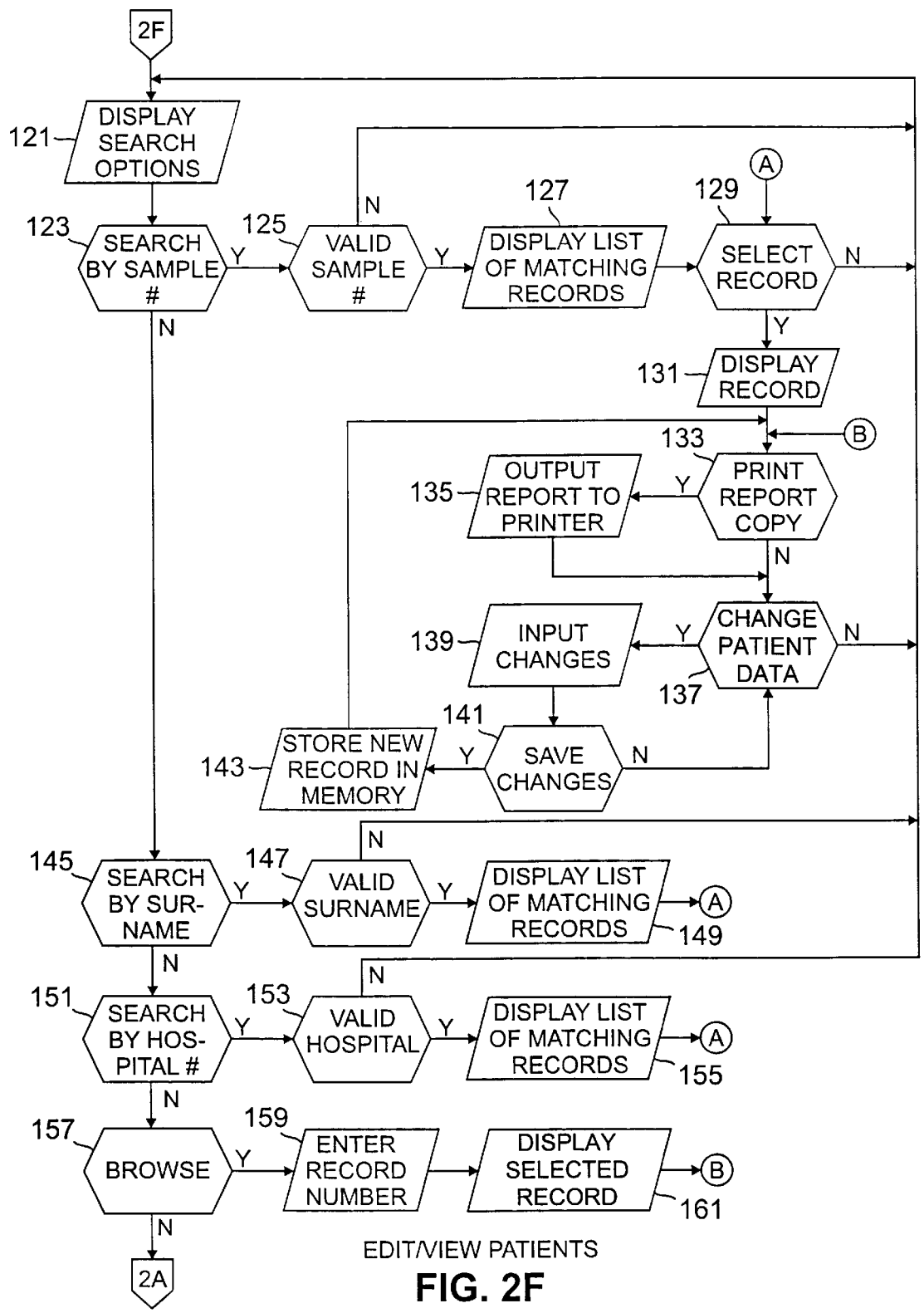
Figure 2G:
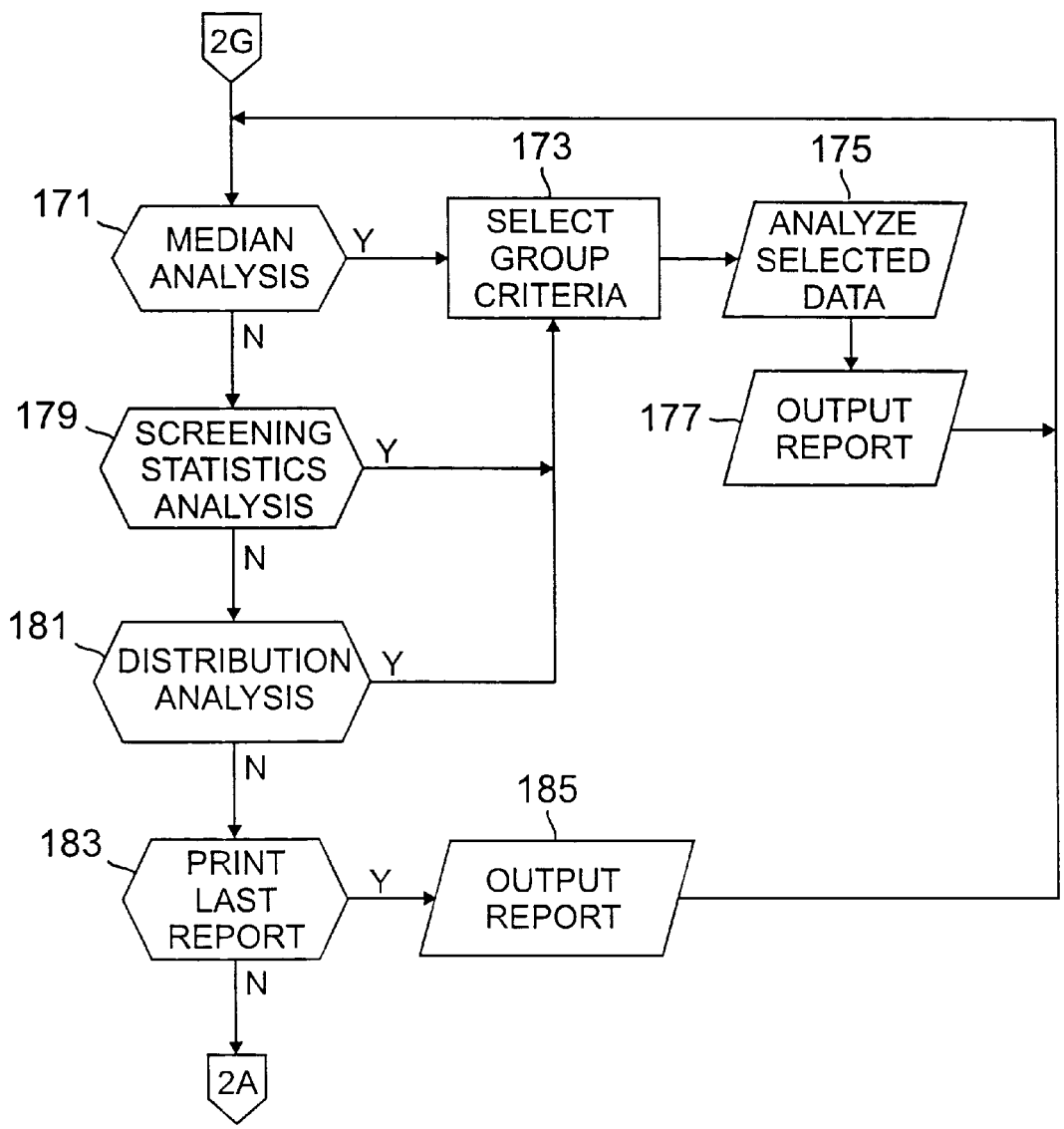
Figure 2H:
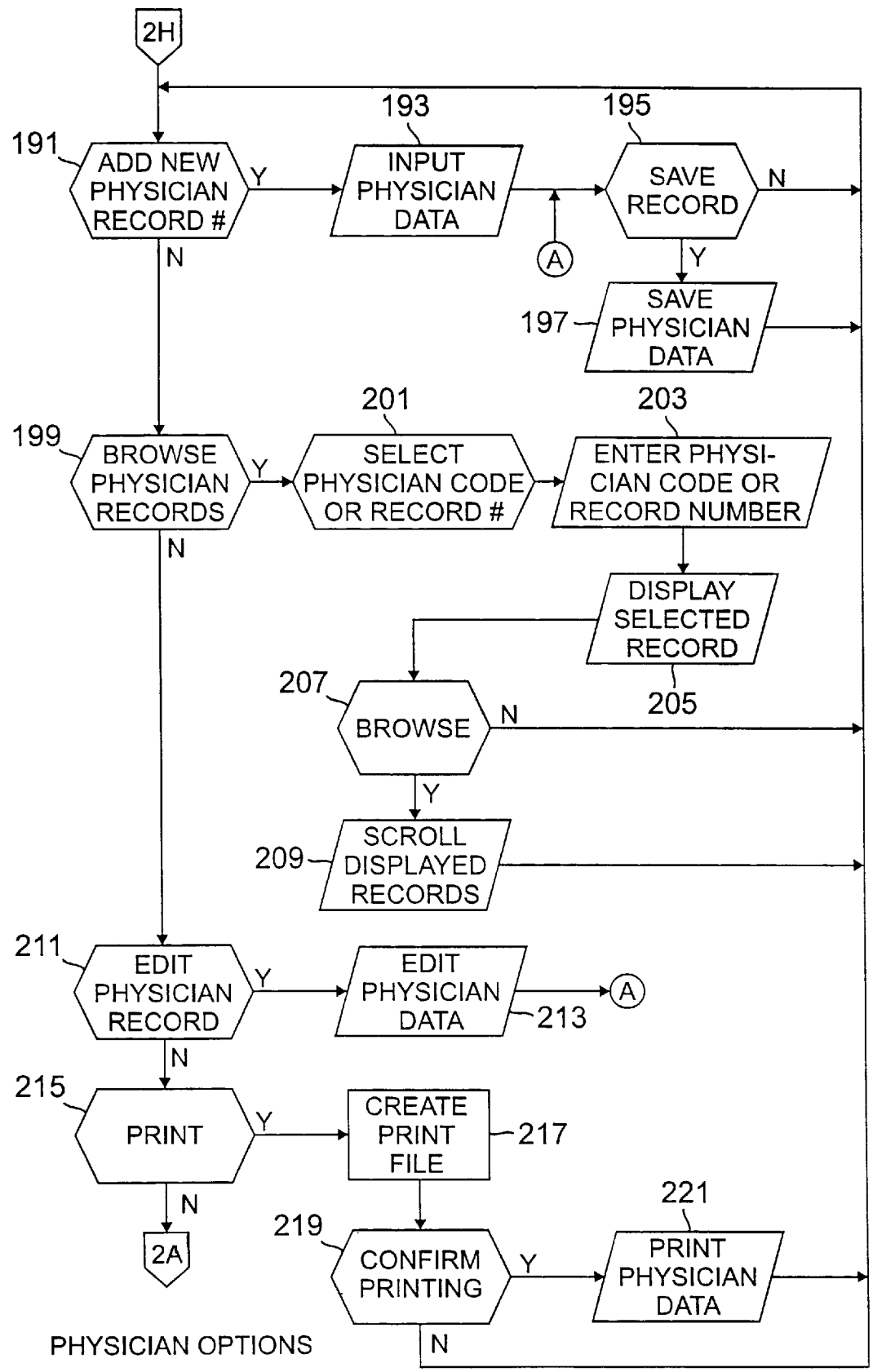
Figure 2I:
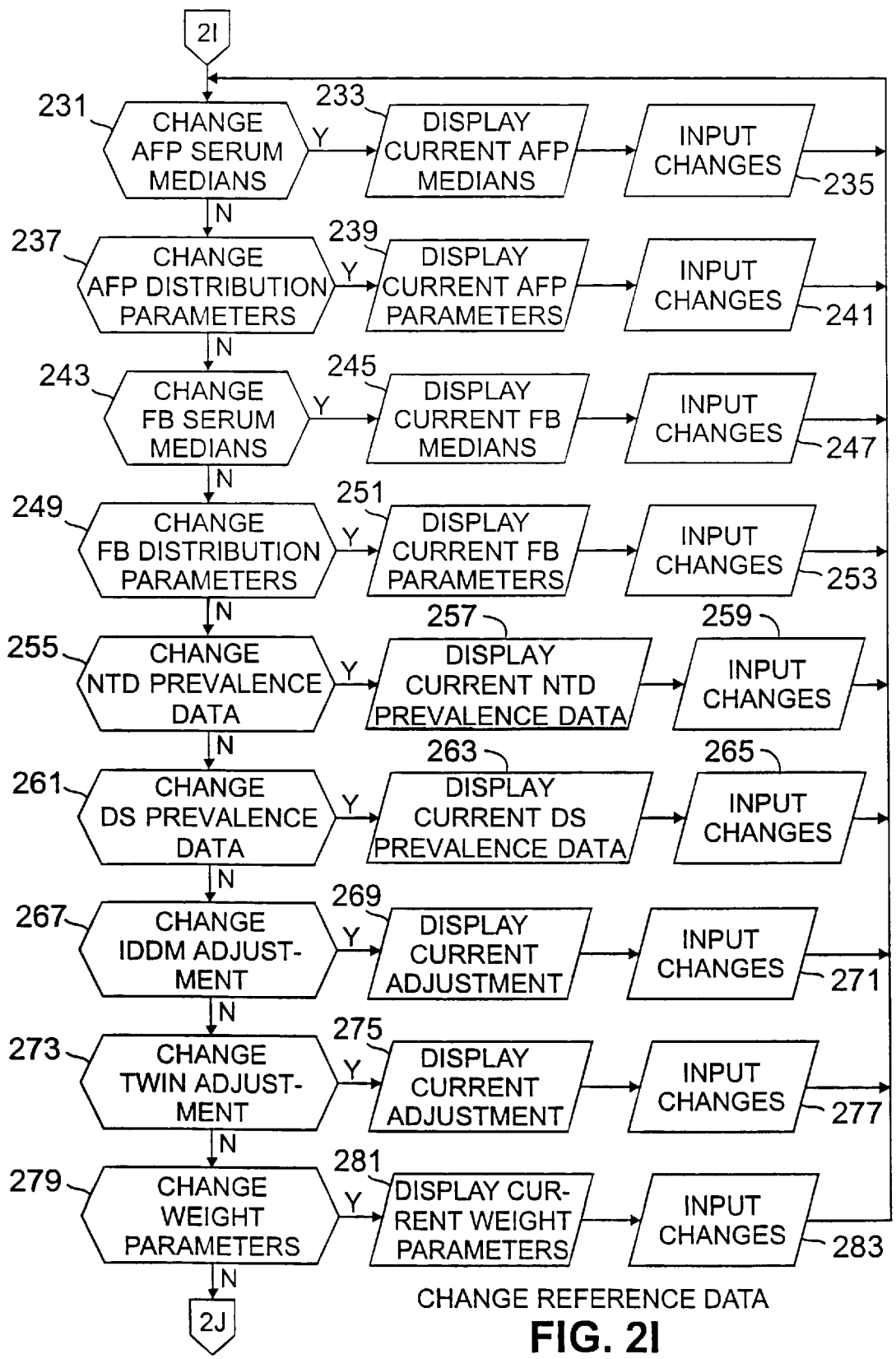
Figure 2K:
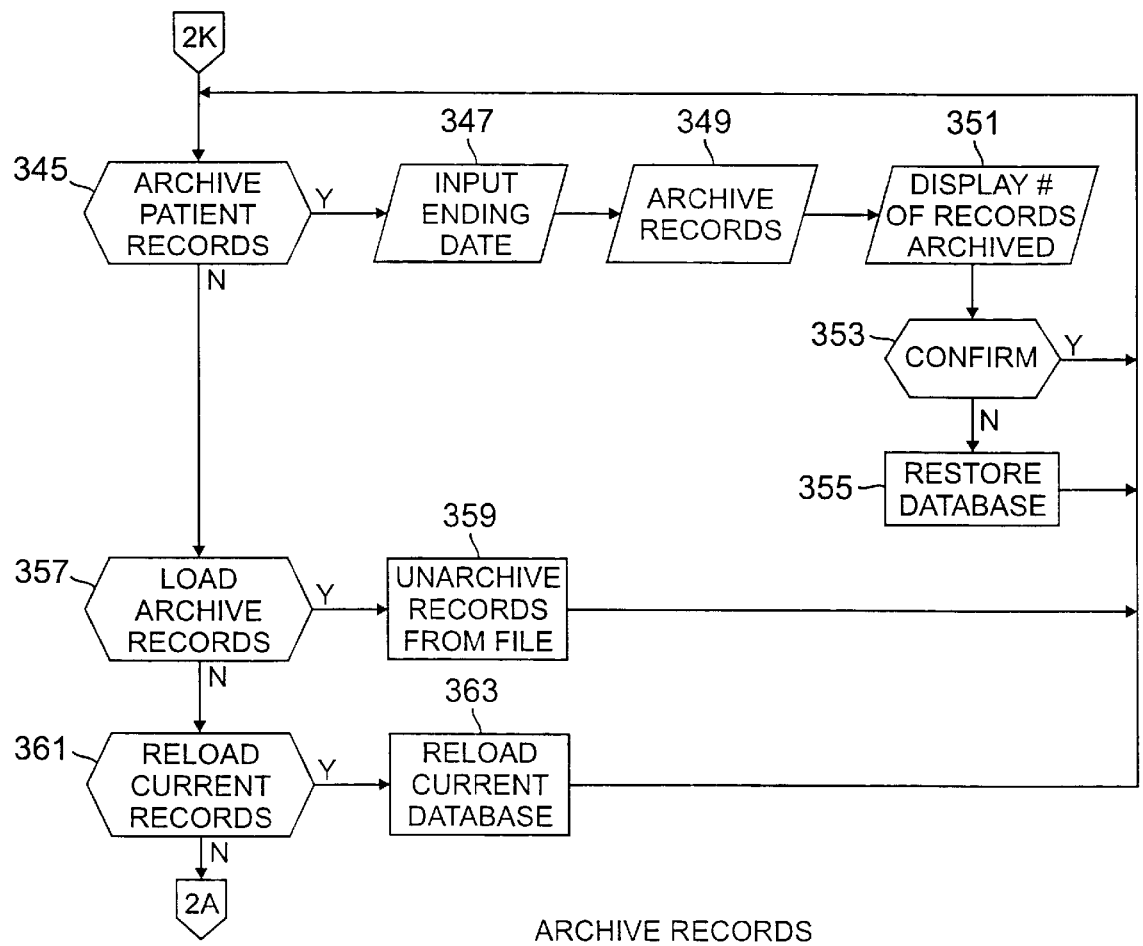
Figure 2L:
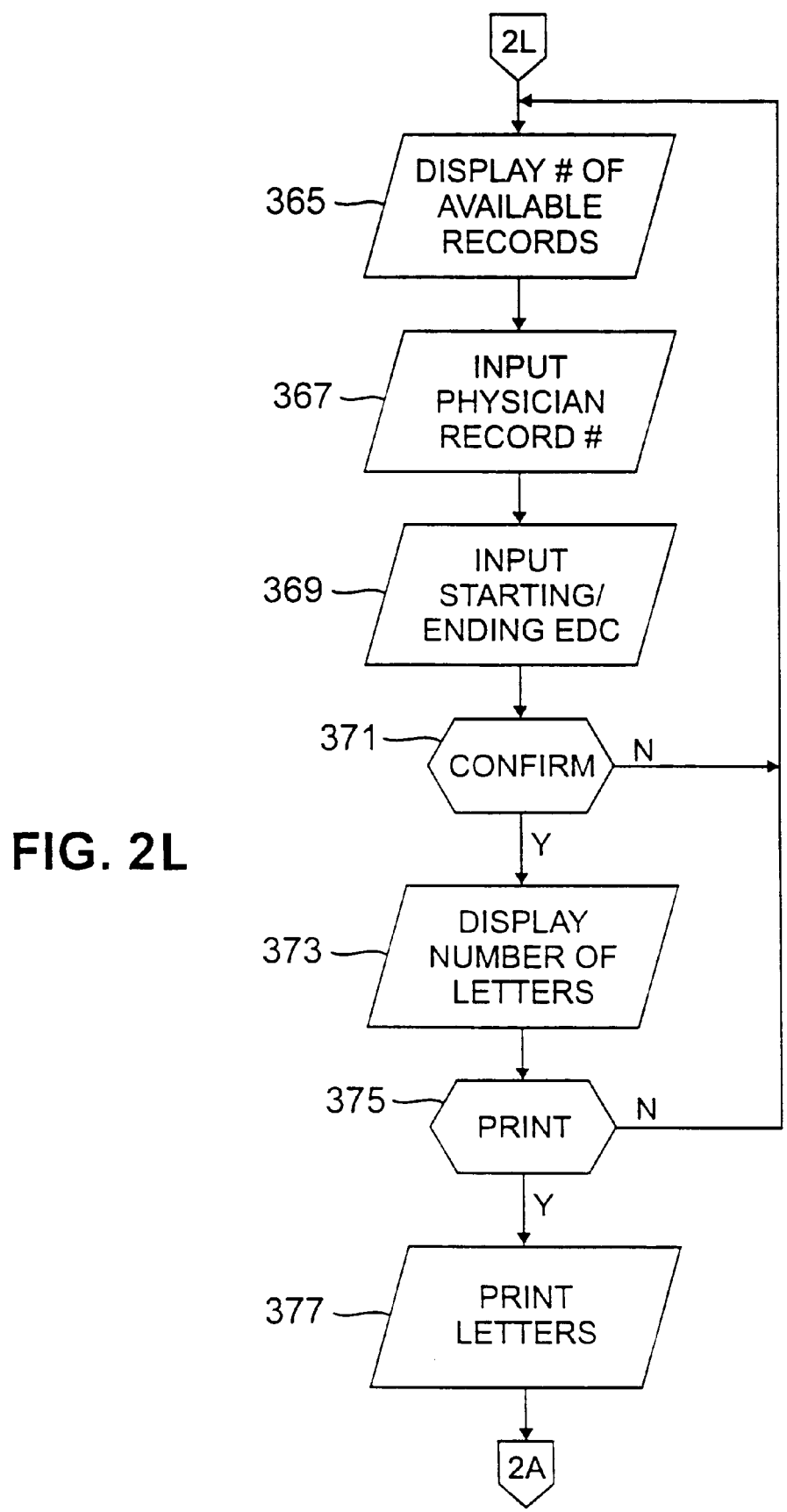

Referring back to FIG. 2A, the user can perform a variety of reporting operations (see decision block 21). Such reporting operations can only be performed if the reports set-up function, i.e. importation of assay data, has been performed in the assay procedure (see decision block 22). Referring to FIG. 2E, the user can calculate screening risks for each patient (see decision block 91). In block 93, the system calculates all necessary information, including multiples of medians (MOMs) and risks for each condition (if applicable). In order to calculate MOMs and risks, reference data is required. The reference data comprises:

the levels of the analytes in pregnant women carrying a fetus with the particular condition ("affecteds"), the levels of the analytes in pregnant women carrying a fetus without the condition ("unaffecteds"), the prevalence of the condition in the overall population, and patients' clinical data.

In addition, each patient record is updated to reflect the patient's analyte levels, MOMs, and risks (see block 95). This information can be viewed and edited in other sections of the program. Each time new assay data is entered into the system, patient risks may be calculated using the above option and the new risks will be added to the file containing all previously calculated risks. When reports are printed, this file may be over-written (see below).

The calculation of MOMs and risks utilizing the normative data, and data from the patient sample is performed in any manner known to those of ordinary skill in the art Preferably, a patient specific risk of carrying a fetus with Down syndrome is calculated using Bayes rule, the patients a priori risk, and the relative frequencies for unaffected and affected pregnancies which are determined by incorporating the patient's quantitative levels on each analyte (free Beta and AFP) along with the patient's gestational age, into the probability density functions developed for the reference data using multivariate discriminant analysis. The multivariate discriminant analysis can be performed on the commercially available computer program statistical package Statistical Analysis System (manufactured and sold by SAS Institute Inc.) or by other methods of multivariate statistical analysis or other statistical software packages known to those skilled in the art.

As known to those of ordinary skill in the art, to determine whether the patient is at increased risk of carrying a fetus with Down syndrome, a cut-off must be established. It is obvious to those skilled in the art that a cut-off established to determine whether a patient is at increased risk of carrying a fetus with Trisomy 13 or Trisomy 18 may also be effective in identifying cases of trisomy 21. This cut-off may be established by the laboratory, the physician or on a case by case basis by each patient. The cut-off level can be based on several criteria including the number of women who would go on for further invasive diagnostic testing, the average risk of carrying a Down syndrome fetus to all the women who go on for further invasive diagnostic testing, a decision that any woman whose patient specific risk is greater than a certain risk level such as 1 in 400 should go on for further invasive diagnostic testing or other criteria known to those skilled in the art. The cut-off level could be established using a number of methods, including: percentiles, mean plus or minus standard deviation(s); multiples of median value; patient specific risk or other methods known to those who are skilled in the art.

The probability density function provides a method for comparing the patient's level of each analyte to a set of reference data. One type of probability density function is set forth below, although as will be obvious to one skilled in the art, other probability density functions will perform similarly, and therefore perform adequately in the present invention.

Formula for Risk of Down syndrome $$\frac{(1/\sqrt{|cov|}) \times \text{Exp}(-.5(X_d - M_d)^T cov^{-1}(X_d - M_d)) \times \text{Prior Risk}}{[(1/\sqrt{|cov|}) \times \text{Exp}(-.5(X_d - M_d)^T cov^{-1}(X_d - M_d)) \times \text{Prior Risk} + (1/\sqrt{|cov|}) \times \text{Exp}(-.5(X_u - M_u)^T cov^{-1}(X_u - M_u)) \times (1 - \text{Prior Risk})}$$

The subscript "a" refers to the affected cases

The subscript "u" refers to the unaffected cases (X–M) is a vector where each element is the level of each variable minus the mean of the variable.

$cov^{-1}$ is the inverse of the pooled covariance matrix of the affected and unaffected of all of the variables in the model $(X-M)^T$ is the transpose of the (X–M) vector.

EXP refers to the exponential function.

|COV| refers to the determinant of the covariance matrix of all the variables in the model for the reference data As obvious to those skilled in the art, individual covariance matrices for unaffected and affected pregnancies can be substituted for the pooled covariance matrix. The formula for the Risk of Down syndrome would then become:

$$\frac{(1/\sqrt{|cov|_d}) \times \text{Exp}(-.5(X_d - M_d)^T cov_d^{-1}(X_d - M_d)) \times \text{Prior Risk}}{[(1/\sqrt{|cov|_d}) \times \text{Exp}(-.5(X_d - M_d)^T cov_d^{-1}(X_d - M_d)) \times \text{Prior Risk} + (1/\sqrt{|cov|_u}) \times \text{Exp}(-.5(X_u - M_u)^T cov_d^{-1}(X_u - M_u)) \times (1 - \text{Prior Risk})]}$$

For the purposes of the discriminant analysis an assumption is made as to the prior probability of Down syndrome in the general unselected population. Generally, the prior probability is approximately 1 in 800. For the multivariate discriminant analysis a decision is made as to what risk cut-off level constitutes a positive test result. For example, if it is desirable to perform further diagnostic tests on a pregnant woman who has a 1 in 400 or greater possibility of carrying a Down syndrome fetus, then when the results of the discriminant analysis indicate that a pregnant woman has a 1 in 400 or greater possibility of carrying a Down syndrome fetus, the pregnant woman is considered to have a positive test result. If a positive test result is indicated, the patient should be counselled about further diagnostic tests to confirm the presence of Down syndrome.

With reference to FIGS. 3–6, a flowchart for a computer program for calculating the reference parameters and specific risk, in a screening protocol utilizing AFP and free Beta as analytes, are shown.

Figure 3:
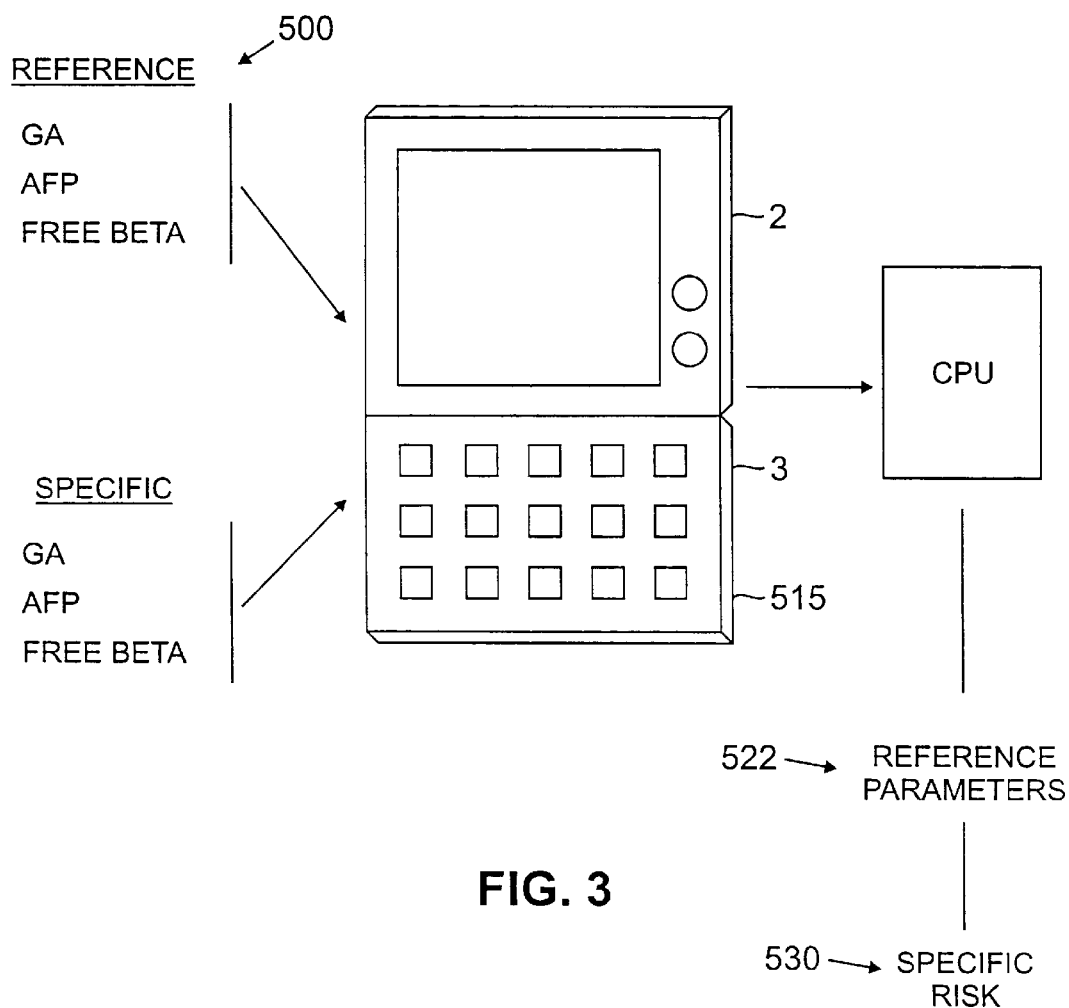
FIGS. 3–6 depict flowcharts for a computer program for calculating the reference parameters and specific risk, in a screening protocol utilizing AFP and free Beta as analytes.

As shown in FIG. 3, the gestational age GA, the level of AFP and the level of free Beta are determined by conventional techniques from affected and unaffected pregnancies in order to develop reference data. A large number of samples are chosen to increase reliability. The measurements for the development of reference parameters are indicated schematically at 500.

Once the reference parameters 522 are calculated by the processing unit 1 after entry via a suitable input device 515, the specific risk 525 for a particular patient can be calculated based on the individual's specific measured marker values, indicated at 530.

Figure 4A:
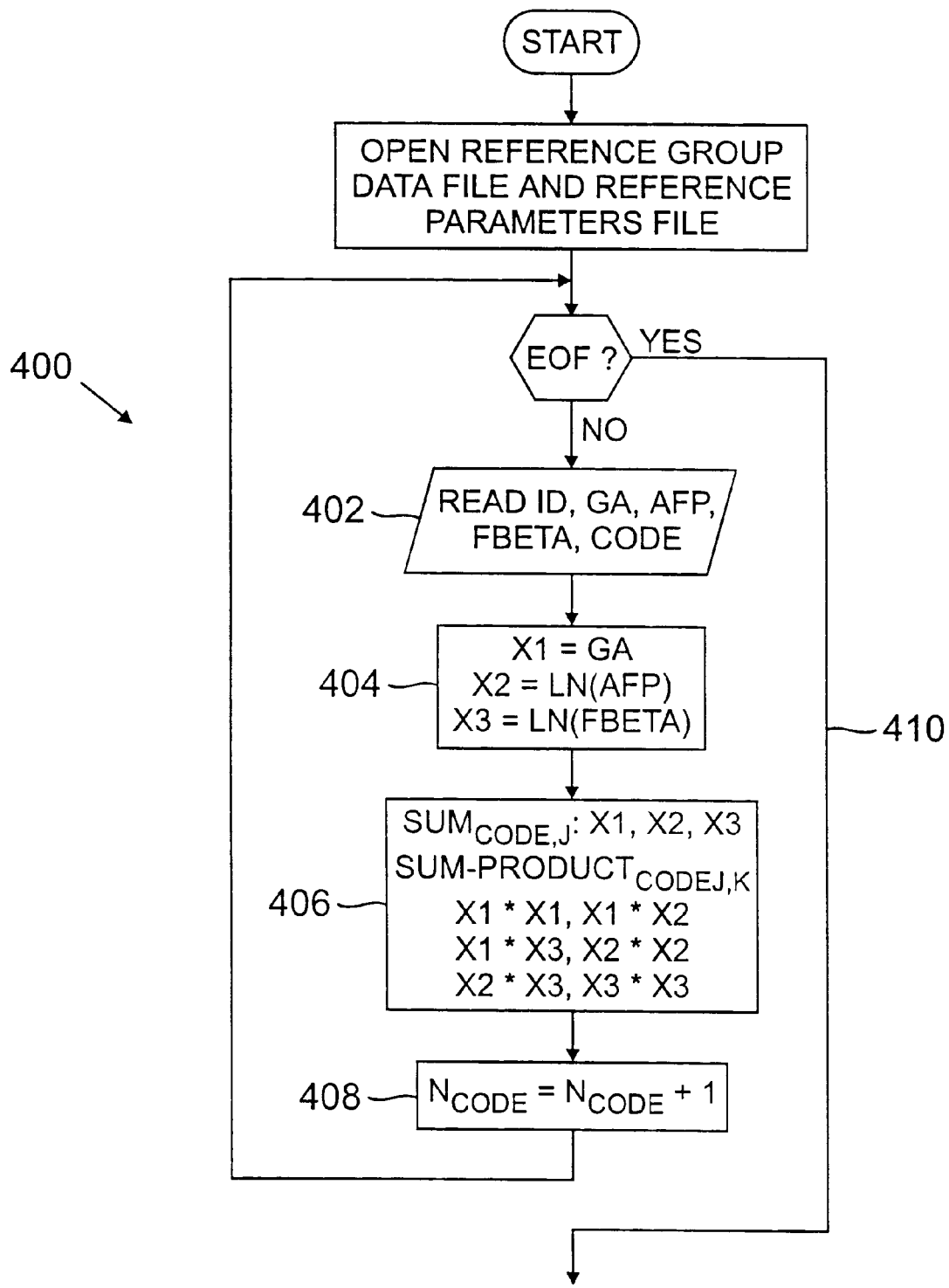
Figure 4B:
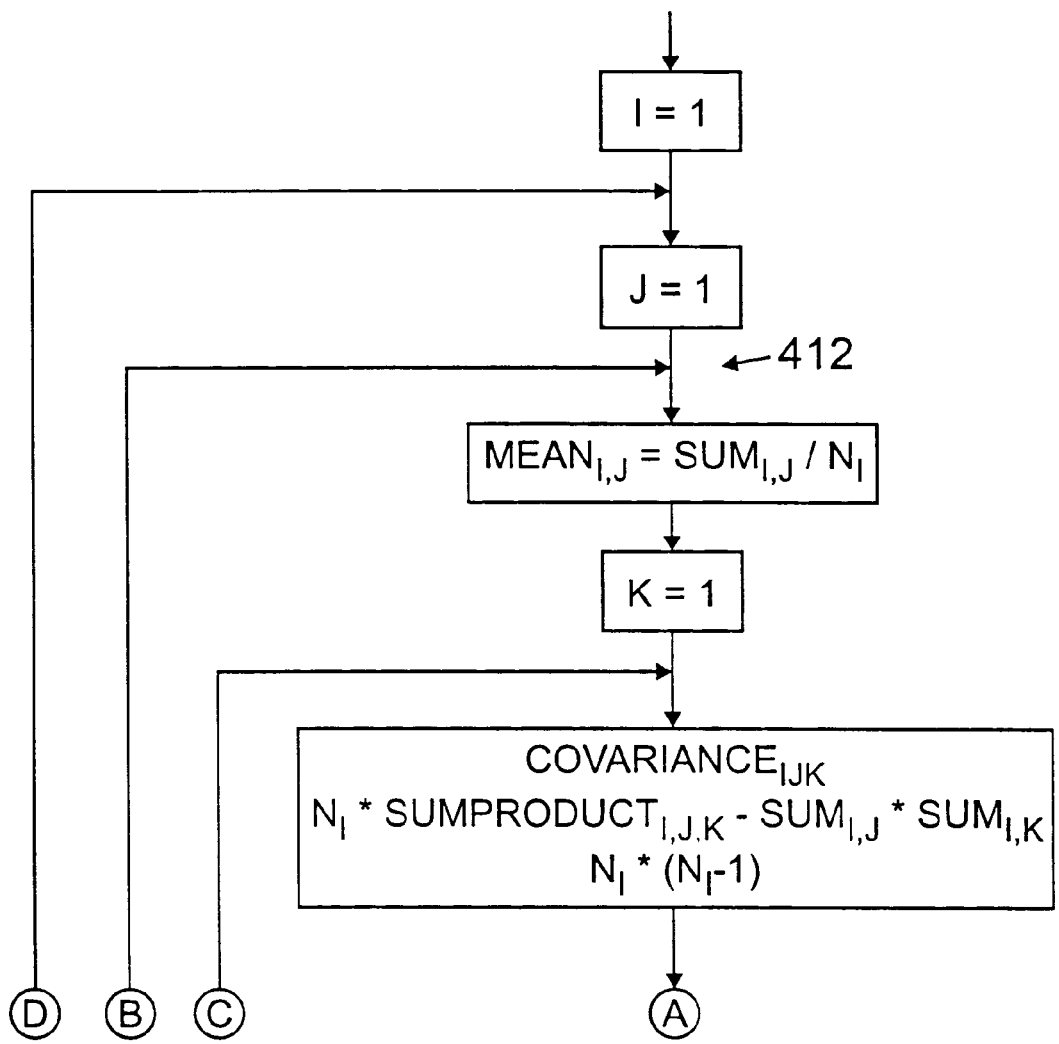
Figure 5A:
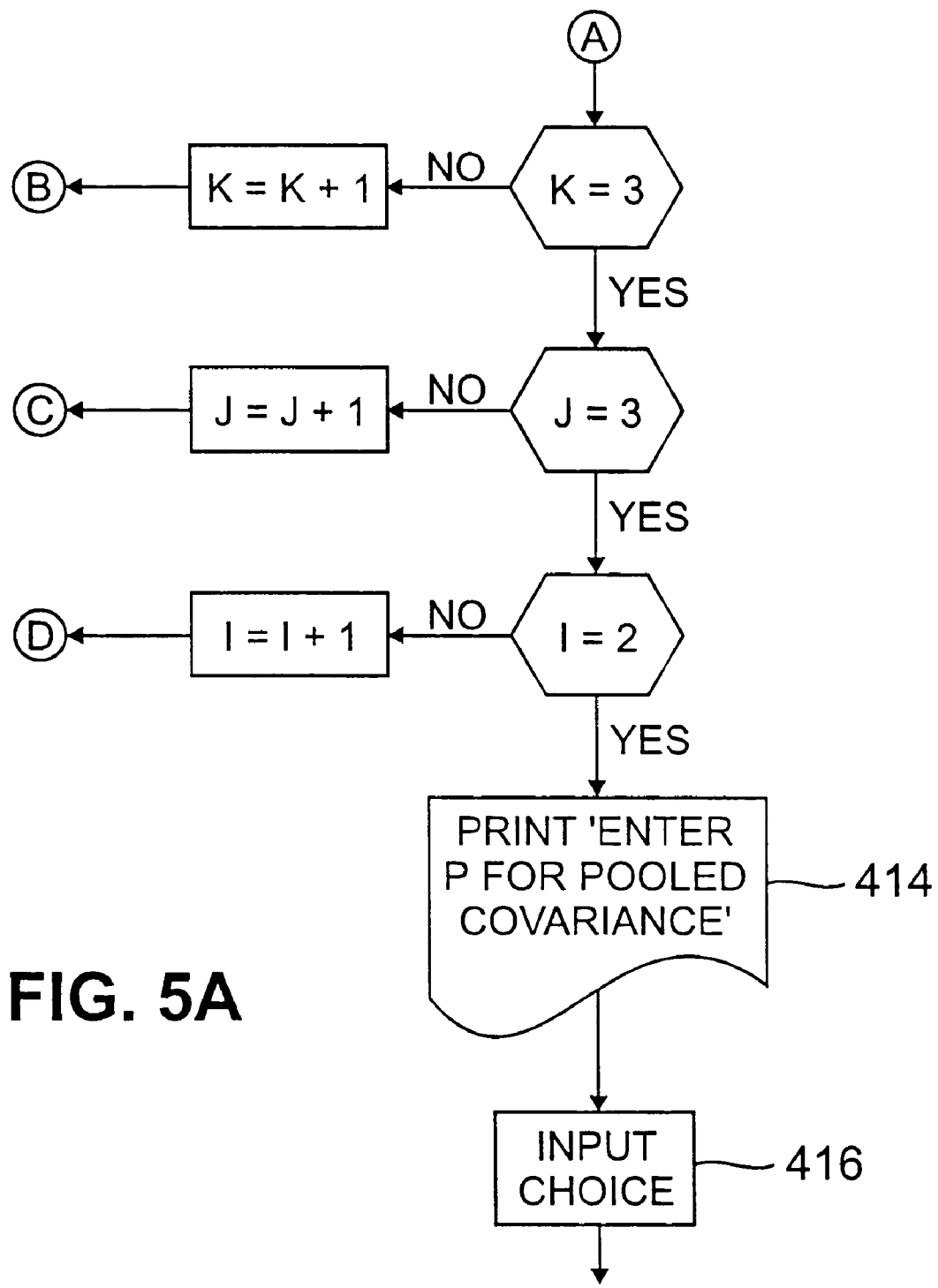
Figure 5B:
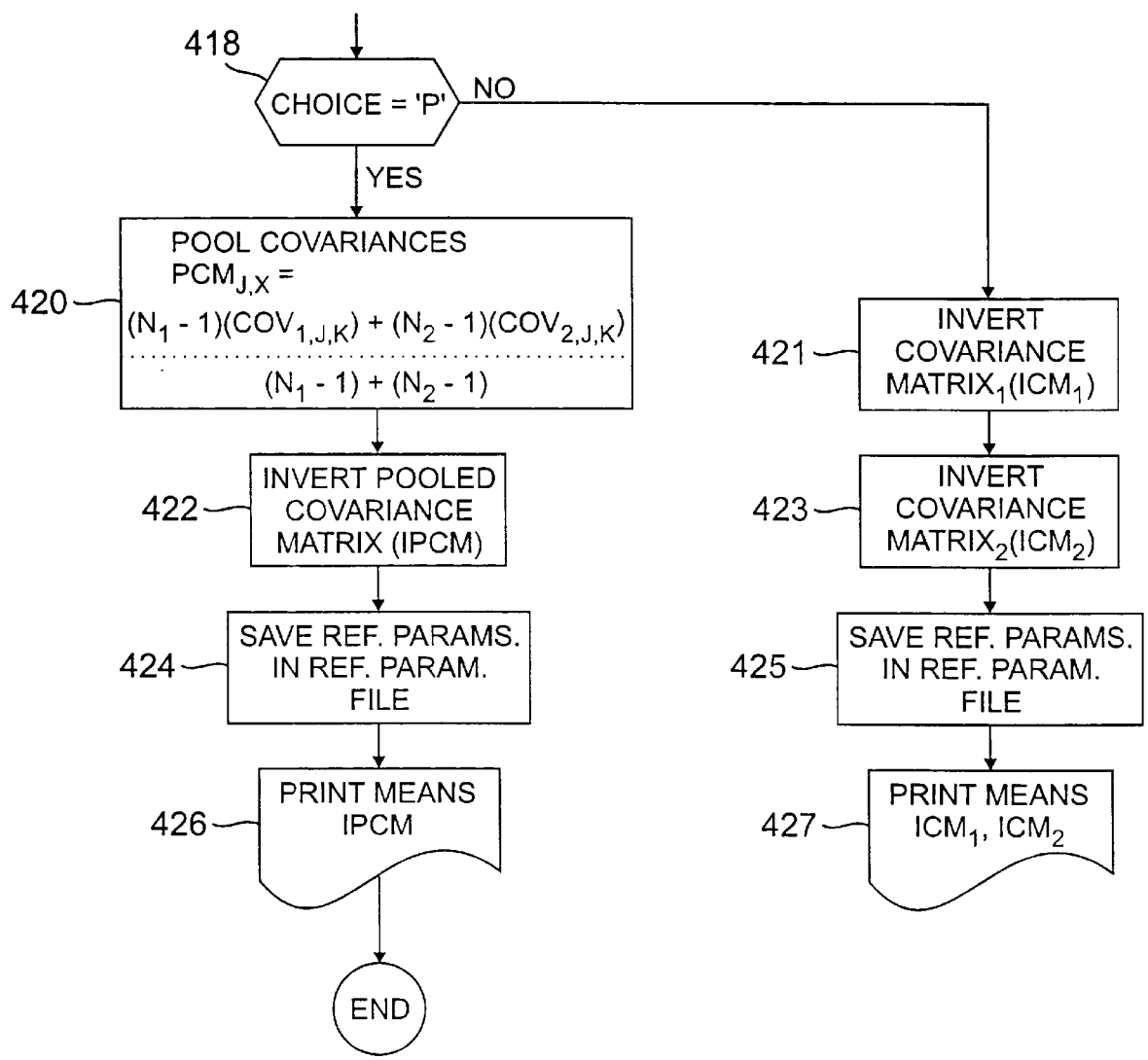
Figure 6:
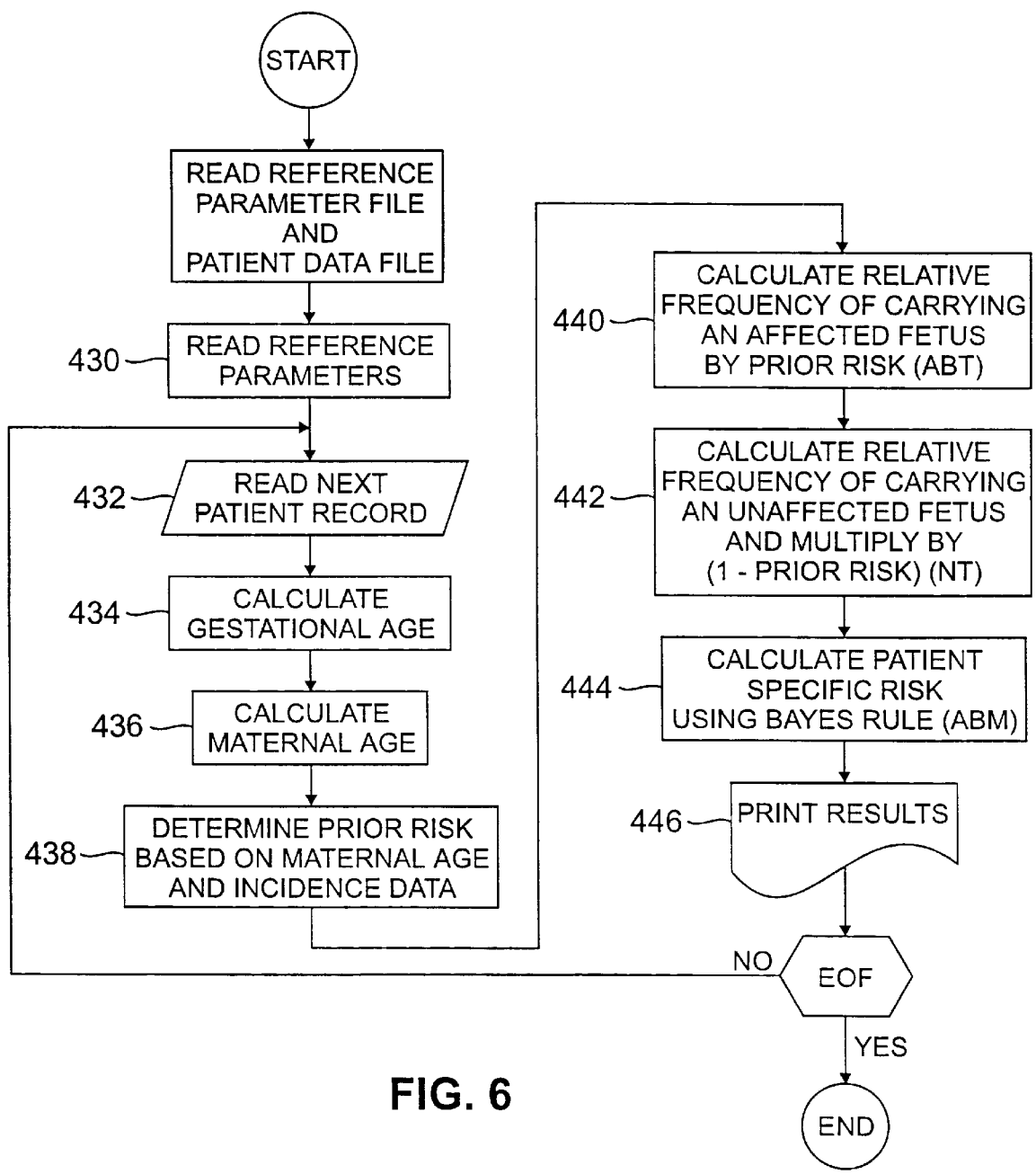

The program for determining the reference parameters is shown in FIGS. 4 and 5 and the program for calculating specific risk is shown in FIG. 6.

With reference now to FIGS. 4 and 5, in a first loop 400, the program reads in identification data ID, gestational age GA, quantities of AFP and free Beta and a CODE indicating whether the pregnancy is affected or unaffected by Trisomy 21 from a reference group in order to develop reference data. This is shown in step 402. In the flowchart, gestational age GA is denoted by variable $X^1$, the log of AFP is given by variable $X^2$ and the log of free Beta is given by $X^3$, as shown in step 404. The sum and sum-product matrices are then determined or calculated as shown in step 406 based upon the quantities $X^1$, $X^2$ and $X^3$. The variable $N_{CODE}$ which count the number of affected and unaffected cases in the reference group is then incremented. Once the loop is terminated, as shown by flow line 410, the means are then calculated through series of loops defined by the quantities I, J and K as indicated by reference numeral 412. In these loops, the covariance matrix is calculated utilizing the sum matrix defined in loop 400 and the sum product matrix calculated in loop 400. After these loops, a choice is made whether to pool or not to pool the covariance matrices for the affected and unaffected. This choice is inputted in steps 414, 416 and 418 the choice is to pool, the covariances are pooled to form pooled covariance matrix as given by step 420, the pooled covariance matrix is inverted resulting in the inverted pooled covariance matrix IPCM as shown at 422, and the means and the inverted pooled covariance matrix are saved in a file and printed out at steps 424 and 426. If the choice is not to pool the covariance matrices, then each of the two covariance matrices are inverted in steps 423 and 425 and the means and the inverted covariance matrices are saved in a file and printed out in steps 425 and 427. These quantities comprise the reference parameters for the calculation of a specific individual's risk of carrying an affected fetus.

With reference to FIG. 6, the reference parameters determined during the execution of the program shown in FIGS. 4 and 5, the reference parameters comprising the means and the inverted pooled covariance matrix, are read in as shown at 430. The specific patient record, including the patient identification, the gestational age GA, AFP and free Beta are then read in as shown at 432. The gestational age is then calculated more specifically at 434, and a maternal age calculation is made at 436. At 438, the prior risk is determined based upon maternal age and incidence data. In the examples discussed below, the result of this calculation is the factor 1/800, a typical number.

At 440, the prior risk times the relative frequency of carrying an affected fetus (ABT) is determined, which is the numerator of the equations (1) or (2) discussed above. At 442 the relative frequency of carrying an unaffected fetus multiplied by (1-prior risk), (NT), is determined, which is the second factor in the denominator of equations (1) or (2) found above. At 444, the specific risk using Bayes Rule is determined, i.e., ABN=ABT/(ABT+NT). (Equations (1) and (2)) At 446, the results are printed, i.e., the patient's specific risk ABN and the patient identification number.

Selection of "Print Special Cases" (see decision block 97) passes control to block 99, and the system can print a list of patients meeting any of the following criteria (see blocks 101 and 103) (categories are selected by the user):

SECOND SAMPLES REPORTED NORMAL
    INCREASED RISK FOR DOWN SYNDROME
    HIGH MATERNAL SERUM AFP
    HIGH AMNIOTIC FLUID AFP
    INSULIN DEPENDENT PATIENTS
    AFP LEVELS BELOW SENSITIVITY
    FREE BETA LEVELS BELOW SENSITIVITY
    GA OUT OF RANGE
    DATA IMPORTED—REPORT NOT PRODUCED

The lists are generated by searching through all patient records in the current set to locate those having data matching one of the above descriptions.

In decision block 105, reports can be created on all acceptable results that were imported and/or all reports requested using the patient search procedure (method described below) (see block 107). Each patient report contains the patient's personal information, MOMs, risks for each condition, and result interpretations. A result interpretation is a textual description of the patient's risk, e.g. normal, elevated, etc. The text for the result interpretations is definable by the user. In decision block 109, the user can opt to have all reports printed (see block 111). Each time the user creates and prints reports the old files containing patient reports and patient risks are over-written. In decision block 113, the user can delete the current report file. This option will delete all analyte levels, patient risks, and patient reports that were produced from the last batch of data that was imported (see block 115). Each patient's record will be restored to the way it was after data entry (see block 117).

Referring to FIG. 2A, the user can perform a variety of search functions (see decision block 23). In such a case, control passes to FIG. 2F. In block 121, available patient records can be searched by sample number, surname, hospital number, or record number. If the user seeks to search based on patient sample number (see decision block 123), the user is asked to input the sample number desired. If a valid sample number is entered, the system will display the Sample Number, Surname, First Name, Hospital Number, and Date Drawn for all patients on file which have a sample number starting with the numbers entered, e.g. records for 333, 33345, 333457 will be displayed if 333 is entered (see block 127). In this embodiment, up to fifteen patient records are listed at one time, and the user can scroll through selected records in a known manner. At this point the user can request to see information regarding a specific patient associated with a displayed record (see decision block 129 and block 131). Once the patient record is displayed, a report copy can be printed (see decision block 133 and block 135). Also, the displayed clinical data can be changed (see decision block 137 and block 139). To change data in block 139, a list of data fields that can be changed will be displayed. A password must be entered before analyte results can be changed. In this embodiment, the user merely scrolls through the data fields in a known manner, and the system prompts the user to enter the new data The new data is used to revise the risk data (if necessary) and the information will then be redisplayed.

At this point, the user can request a report copy, change data again, or save any changes (see decision block 141 and block 143). To obtain a revised report the changes must be saved. At this point, further searching can be performed by the user (see block 121).

The user can search available records by surname (see decision block 145). If the surname exists in the available files (see decision block 147), the system will display the Surname, First Name, Sample Number, Hospital Number, and Date Drawn for all patients on file with the Surname entered (see block 149). The user can then select a specific patient associated with a listed record for display (see decision block 129 and block 131). Once the patient record is displayed, the user has the option of obtaining a report copy or changing data as before.

The user can search for records based on hospital number (see decision block 151). If the hospital number exists in the available files (see decision block 153), the system will display the Hospital Number, Surname, First Name, Sample Number, and Date Drawn for all patients on file having the selected hospital number (see block 155). The user can then select a specific patient associated with a listed record for display (see decision block 129 and block 131). Once the patient record is displayed, the user has the option of obtaining a report copy or changing data as before.

The user may also browse through the available patient records (see decision block 157). In block 159, the user is prompted to enter a record number. The record number is a number assigned by the system which corresponds to the order in which the patient record was entered into the system, i.e. record number 1 is the first record ever entered into the system. In block 161, the patient record selected is displayed. The user can "scroll" or "page" through the patient records as desired. As before, once a desired patient record is displayed, the user can request a report copy or change data (see decision block 133).

Referring back to FIG. 2A, the user can have a statistical analysis performed upon the data within the patient records (see decision block 24). In this option, the user can request a median analysis report, screening statistics report, or distribution analysis report. Upon selection of statistical reports by the user, control shifts to FIG. 2G. In decision block 171, the user can request a median analysis report. In median analysis, the system requests the starting/ending specimen receipt dates, ethnic group, and other criteria (see block 173). The system then analyzes all the data that matches these criteria and generates statistics for the levels of maternal serum AFP, amniotic fluid AFP, and/or maternal serum free Beta in the patient samples by gestational week for each ethnic group (see block 175). The printed report (see block 177) for each gestational week will include the:

Number (number of samples received for that week)
    Median Days (median number of days for samples at that week)
    Observed Median (AFP or free Beta median for that week)
    At Median Days (regressed median at Median Days)
    At Start of Week (regressed median at the beginning of the week)
    Current Medians (median currently entered into the system in the setup option—see below)
    Percent Difference (the difference between the Observed and Current Median)

In decision block 179, the user can request a screening statistics report. In a like manner to the median analysis, the system requests the starting/ending specimen receipt dates, ethnic group, and other criteria (see block 173). The system then analyzes all the data that matches that criteria and generates statistics for each possible report interpretation (e.g. Normal, Elevated, etc.) for ONTD screening, Down syndrome screening with AFP only, and Down syndrome screening with AFP/free Beta for each ethnic group (see block 175). The printed report (see block 177) will include the number of specimens for each report interpretation and the percentage of the total specimens at that interpretation.

The user can also perform a distribution analysis (see decision block 181). In a like manner to the median analysis, the system requests the starting/ending specimen receipt dates, ethnic group, and other criteria (see block 173). The system then analyzes all the data that matches that criteria and generates statistics for each ethnic group (see block 175). The printed report (see block 177) for each ethnic group will include:

Number (number of specimens)
Obs. Mean (observed mean)
Exp. Mean (current mean entered in the system setup option—see below)
Obs. SD (observed standard deviation)
Percent Diff Obs. & Exp. Mean (difference between the Observed and the Expected Mean)
Number (>0.0)
Obs. Mean Log (log of the Observed Mean)
Exp. Mean Log (log of the Current Mean)
Obs. SD Log (log of the Observed Standard Deviation)
Z Score The user can also request an additional copy of the latest report generated (see decision block 183 and block 185).

Referring back to FIG. 2A, the user can perform a variety of functions to enter and to search records of participating physicians (see decision block 25). Control passes to FIG. 2H, where in decision block 191 the user can opt to enter a new physician record. An example of the information entered in block 193 is shown in Table III.

TABLE III

Code (Used as Index)
Physician Name
Info Line 1
Info Line 2
Info Line 3
Info Line 4
Send Copy To
Number of Reports Each physician is assigned a unique code (e.g., a four digit code) by the user for identification purposes. The physicians telephone number and address can be entered into the "Info" lines. The "Send Copy To" field indicates that copies of reports on all patients from this physician should also be sent to a second physician. The physician code of the second physician is entered here. The "Number of Reports" field indicates the number of copies of each patient report requested by the physician (up to 5). When the data for all fields is entered, in decision block 195 the user may save the record, and the physician's name is added to the physician database (see block 197). The system will assign a unique record number to each physician which corresponds to the order in which the physician record was entered into the system.

Referring to decision block 199, the user can search physician records by physician code or record number (see decision block 201 and block 203 and 205). The record number is a number assigned by the system which corresponds to the order in which the physician record was entered into the system, i.e. record number 1 is the first record ever entered into the system. The user can also browse the available records (see decision block 207 and block 209).

The user can edit any of the physician records (see decision block 211 and block 213). The user can also print any selected patient records based on physician number, for example (see decision blocks 215 and 219 and blocks 217 and 221). The user can also delete a physician record (record will be removed from current database) or retrieve a record previously deleted (record will be returned to the current database) (not shown in flowcharts).

Referring back to FIG. 2A, the user may enter reference data for use in the computations described above (see decision block 26). In such a case, control is passed to FIG. 2I. In decision block 231, the user has the option of entering AFP medians, which are needed in the calculation of multiples of the median and patient risks. In block 233, the user is shown current or default settings for AFP serum medians for each ethnic group for each gestational week. In block 235, the user can enter any changes to the displayed values. The user may also enter or change AFP medians for amniotic fluid (not shown in flowcharts).

In decision block 237, the user can display and change AFP distribution parameters. In block 239, the AFP distribution parameters are displayed as the mean and standard deviation (in logs—the base is selected by the user in the system setup option) of normal pregnancies and those with open spina bifida, and anencephaly. Upper and lower MOM bounds are also displayed. In block 241, the user can input new AFP distribution parameters.

In decision block 243, the user can display and change free Beta medians similarly to the change of AFP medians (described above; see blocks 245 and 247). In decision block 249, the user can display and change Down Syndrome distribution parameters. In block 251, the system displays the mean and standard deviation for AFP and free Beta for normal specimens and those with Down Syndrome. The system also displays a correlation between the AFP and free Beta values (in logs). AFP and free Beta upper and lower MOM bounds are also displayed. These values can also be changed (see block 253).

In decision block 255, the user can display and change NTD prevalences (e.g., as a ratio per 10,000 live births). In this embodiment, the system displays the prevalence of open spina bifida and anencephaly for each ethnic group, for patients with a previous NTD, and for insulin dependent patients. Likewise, these values can be changed (see block 259). In decision block 261, Down Syndrome prevalence data can be displayed and changed upon request of the user. In block 263, the system displays the Down Syndrome prevalence for each maternal age and for patients with previous Down Syndrome pregnancies. The Down Syndrome prevalence data can then be changed (see block 265).

The AFP and free Beta medians are needed to calculate multiples of the median, a procedure which is known to those skilled in the art. The AFP/free Beta distribution parameters and the NTD/DS prevalence data are necessary to calculate risks for Anencephaly, Open Spina Bifida, and Down Syndrome. The user may also choose the method of interpolating medians over the range of gestational weeks acceptable for specimens (not shown in flowchart).

An adjustment factor can be entered for patients with Insulin Dependent Diabetes Melitis (IDDM) if desired by the user. The adjustment factor is used by the system to compensate for lower AFP levels of women with this condition (see decision block 267 and blocks 269 and 271).

The user may enter an adjustment factor for patients with twin pregnancies (see decision block 273 and blocks 275 and 277). Since each fetus will produce the same analytes (e.g. AFP, free Beta), the adjustment factor is used by the system to compensate for the higher analyte levels found in the bloodstreams of women with twin pregnancies.

The user can choose to change the parameters used to adjust MOMs and risks for maternal weight (see decision block 279 and blocks 281 and 283). Since women with different weights will have different blood volumes, the analyte levels found in heavier women may be lower due to greater blood volume and the analyte levels found in lighter women may be higher due to lower blood volume. The user inputs changes to the parameters shown below. The maternal weight adjustment factor is computed as follows:

| | |
|---|---:|
| Intercept: | 0.612000 |
| Slope | −0.00952 |
| Min Weight | 40.0 kg |
| Max Weight | 125.0 kg | ln (Maternal Weight Factor)=a+b·(weight)

where a=intercept; and b=slope

Adjusted MOM=MOM/Maternal Weight Factor

The numbers shown for intercept, slope and minimum and maximum weight are given as examples. If a patient's weight is less than the minimum weight, the minimum weight is used in calculating the adjusted MOM. If a patient's weight is greater than the maximum weight, the maximum weight is used in calculating the adjusted MOM. If intercept and slope are set equal to zero, no maternal weight adjustment will take place.

Those skilled in the art will recognize that MOMs as a statistical measure may be replaced by other methods of presenting result data. New formulas may also be developed which more precisely adjust patient results for differences in maternal weight. The scope of the invention should also encompass any changes in the method of adjustment for maternal weight Referring to FIG. 2J, the user has the option of defining certain features and parameters within the system including units of measurement, log base (used in result calculations), cut-off levels for increased risk results, below sensitivity limits for AFP/free Beta, range of gestational weeks acceptable for specimens, order of listing information fields in the patient data entry screen, definition of patient identification codes (sample number and hospital number), date format, printer type, printer paper size, report format (choice of 4) and text to appear on patient reports as the header and the signature line.

The user can choose to modify the descriptions which classify the patient's ethnic group (see decision block 303 and blocks 305 and 307). The order in which these descriptions are entered determines the ethnic group number used in the data entry process. The screening medians for AFP/free Beta for each ethnic group may be set uniquely or set to match an existing ethnic group. This system will enable the user to adjust for different analyte levels in different ethnic groups.

The user has the option of defining the text of the result interpretations which appear in each patient's report (see decision block 327). The report interpretations include a category name, e.g. Normal, Elevated, and two lines of text.

The user may change the security passwords used by the system (see decision block 337). The System Password is used each time the system is entered. The Supervisor Password is used to change system parameters, reference data, or patient results.

If the user does not wish patient records prior to a given date to be used in the current database, these records may be moved (or "archived") to a computer file specified by the user (see FIG. 2A, decision block 27). Control passes to FIG. 2K. The user may later access records which have been previously archived (see decision block 357) and use these records as the current patient database without loss of the existing database (see decision block 361).

The system enables the user to print letters to selected physicians which request outcome information on their patients' pregnancies (see FIG. 2A, decision block 28). Control passes to FIG. 2L. The user will be asked to enter the physician's record number and the starting and ending EDC date for which outcome letters should be generated (see blocks 367 and 369). The information requested by the letters includes:

results of diagnostic testing (if any), baby's sex and birth weight, delivery date, termination date, or fetal loss date, and pregnancy outcome.

The foregoing describes the use of the system of the present invention in a screening protocol for fetal Neural Tube Defects, Ventral Wall Defects, and/or Down Syndrome. However, as will be recognized by those of ordinary skill in the art, the system of the present invention may be utilized in a screening protocol for other fetal chromosomal abnormalities including, but not limited to, Turner's Syndrome and Edwards Syndrome and Trisomy 13. These conditions may be screened for in addition to NTDs, VWDs, and DS, or instead of NTDs, VWDs, and DS. For example, the system of the present invention may be utilized in a screening protocol for fetal Turners Syndrome by configuring the system to accept and report, data relating to the Turners Syndrome in the manner described above with reference to DS.

Further, as will be recognized by those of ordinary skill in the art, it is possible to use the system of the present invention in a screening protocol performed prior to a woman's conception. An embodiment of the present invention may also be utilized in the management and operation of a newborn screening protocol.

The above is a detailed description of particular embodiments of the invention. The full scope of the invention is set out in the claims that follow and their equivalents. Accordingly, the claims and specifications should not be construed to unduly narrow the full scope of protection to which the invention is entitled.

What is claimed is:

1. A digital computer system in a clinical testing laboratory having assay equipment for assaying free Beta in a biological sample obtained from a pregnant patient and utilizing other patient data and reference data, the computer system comprising:

input means for inputting patient data for a pregnant patient into an electronic memory;

a processor for creating an individual record for each patient in response to said patient data;

said processor assigning specific accession numbers for each specimen, creating an assay format for a biological sample, and interfacing with the assay equipment to control the assaying of said biological sample for free Beta;

means for electronically communicating results from the assaying for free Beta into said memory in machine readable form;

said processor reading said assay results and, using said assay results, patient data, and reference data, calculating a patient specific risk that the patient is carrying a fetus having a designated defect;

and said processor creating a first patient report in machine readable form utilizing said patient record, said assay results and said patient specific risk; and means for transmitting said patient report to an output device to produce a second patient report in human readable form.

2. The system of claim 1 wherein the assaying of the biological sample further comprises an analysis of the biological sample selected from the group consisting of: recombinant DNA technology; in-situ PCR; immunogold-silver techniques and immunological assays utilizing antibody reactions.

3. A digital computer system in a prenatal screening laboratory having assay equipment for assaying free Beta in a biological sample obtained from a pregnant patient, and utilizing other patient data and reference data, the computer system comprising:

input means for inputting patient data into an electronic memory;

a processor for creating an individual record for each patient in response to said patient data;

said processor assigning specific accession numbers for each specimen creating an assay format for a biological sample and interfacing with the assay equipment to control the assaying of said biological sample for free Beta;

means for electronically communicating results from the assaying for free Beta into said memory in machine readable form;

said processor reading said assay results and, using said assay results, patient data, and reference data, calculating a patient specific risk that the patient is carrying a fetus having a designated defect;

and said processor creating a first patient report in machine readable form utilizing said patient record, said assay results and said patient specific risk;

means for transmitting said patient report to an output device to produce a second patient report in human readable form.

4. The system of claim 3 wherein the calculation of a patient specific risk compares the level of free Beta in the biological sample to reference data including the level of free beta, at various gestational ages, in: (1) pregnant women carrying Down syndrome fetuses and (2) pregnant women carrying normal fetuses.

5. The system of claim 3 configured to enable the system to be utilized by multiple users.

6. A method of operating a digital computer in a prenatal screening laboratory having assay equipment for assaying free Beta in a biological sample obtained from a pregnant patient, the method comprising:

inputting patient data into an electronic memory;

processing said patient data to create an individual record for each patient in response to said patient data;

creating an assay format for a biological sample;

interfacing with the assay equipment to control the assaying of said biological sample for free Beta;

electronically communicating results from the assaying for free Beta into said memory in machine readable form;

processing said assay results and, using said assay results, patient data, and reference data, calculating a patient specific risk that the patient is carrying a fetus having a designated defect;

creating a first patient report in machine readable form utilizing said patient record, said assay results and said patient specific risk; and transmitting said patient report to an output device to produce a second patient report in human readable form.

7. The method of claim 6 wherein the calculation of a patient specific risk compares the level of free Beta in the biological sample to reference data including the level of free beta, at various gestational ages, in: (1) pregnant women carrying Down syndrome fetuses and (2) pregnant women carrying normal fetuses.

8. The method of claim 7 wherein the biological sample is further assayed for AFP and wherein the calculation of a patient specific risk additionally compares the level of AFP in the biological sample to reference data including the level of AFP, at various gestational ages, in: (1) pregnant women carrying Down syndrome fetuses and (2) pregnant women carrying normal fetuses.

9. The method of claim 7 wherein the biological sample is further assayed for PAPP-A and wherein the multivariate calculation of a patient specific risk additionally compares the level of PAPP-A in the biological sample to reference data including the level of PAPP-A, at various gestational ages, in: (1) pregnant women carrying Down syndrome fetuses and (2) pregnant women carrying normal fetuses.

10. The method of claim 6 wherein calculating a patient specific risk for each patient incorporates data from ultrasonic scanning of the fetus.

11. The method of claim 10 wherein calculating a patient specific risk incorporates data from ultrasonic scanning of the ratio of the biparietal diameter to femur length of the fetus.

12. The method of claim 10 wherein calculating a patient specific risk incorporates data from ultrasonic scanning of the nuchal folds of the fetus.

13. The computer system of claim 1, further comprising:

an inventory control system for managing inventory, and means for interfacing the assay equipment with the inventory control system to enable the inventory control system to update inventory records after the assaying of a biological sample.

14. The computer system of claim 1, further comprising:

a system for organizing and maintaining billing and financial data, and means for interfacing said processor and the system for organizing and maintaining billing and financial data to update laboratory billing and financial records and create a patient billing record.

15. The computer system of claim 3, further comprising:

an inventory control system for managing inventory, and means for interfacing the assay equipment with the inventory control system to enable the inventory control system to update inventory records after the assaying of a biological sample.

16. The computer system of claim 3, further comprising:

a system for organizing and maintaining billing and financial data, and means for interfacing said processor and the system for organizing and maintaining billing and financial data to update laboratory billing and financial records and create a patient billing record.

17. The method of claim 6, further comprising interfacing the assay equipment with an inventory control system to enable the inventory control system to update inventory records after the assaying of a biological sample.

18. The method of claim 6, further comprising interfacing the processor with a system for organizing and maintaining billing and financial data to update laboratory billing and financial records and create a patient billing record.

* * * * *